(12) United States Patent
Nickisch et al.

(10) Patent No.: US 8,334,375 B2
(45) Date of Patent: Dec. 18, 2012

(54) METHODS FOR THE PREPARATION OF DROSPIRENONE

(75) Inventors: Klaus Nickisch, Berlin (DE); Kirk Acosta, San Antonio, TX (US); Bindu Santhamma, San Antonio, TX (US)

(73) Assignee: Evestra, Inc., San Antonio, TX (US)

( * ) Notice: Subject to any disclaimer, the term of this patent is extended or adjusted under 35 U.S.C. 154(b) by 292 days.

(21) Appl. No.: 12/752,859

(22) Filed: Apr. 1, 2010

(65) Prior Publication Data

US 2010/0261896 A1 Oct. 14, 2010

Related U.S. Application Data

(60) Provisional application No. 61/168,261, filed on Apr. 10, 2009, provisional application No. 61/240,413, filed on Sep. 8, 2009.

(51) Int. Cl.
*C07J 53/00* (2006.01)

(52) U.S. Cl. .......................................... 540/15; 552/513

(58) Field of Classification Search .................... 540/15; 552/513
See application file for complete search history.

(56) References Cited

U.S. PATENT DOCUMENTS

| | | | |
|---|---|---|---|
| 4,129,564 | A | 12/1978 | Wiechert et al. |
| 4,501,695 | A | 2/1985 | Van Rheenen |
| 6,121,465 | A | 9/2000 | Mohr et al. |
| 6,933,395 | B1 | 8/2005 | Mohr et al. |
| 7,319,154 | B2 | 1/2008 | Seilz et al. |
| 7,585,971 | B2 | 9/2009 | Costantino et al. |
| 2005/0019245 | A1 | 1/2005 | Koulikov |
| 2005/0090663 | A1 | 4/2005 | Franczyk et al. |
| 2007/0049747 | A1 | 3/2007 | Seilz et al. |
| 2008/0076915 | A1 | 3/2008 | Cabri et al. |
| 2008/0200668 | A1 | 8/2008 | Soros et al. |
| 2008/0207575 | A1 | 8/2008 | Costantino et al. |
| 2009/0023914 | A1 | 1/2009 | Pontiroli et al. |
| 2010/0311702 | A1 | 12/2010 | Klar et al. |

FOREIGN PATENT DOCUMENTS

| | | |
|---|---|---|
| CA | 1065849 | 11/1979 |
| CN | 101092443 | 12/2007 |
| EP | 0099854 | 2/1984 |
| EP | 1571153 | 9/2005 |
| EP | 1903051 | 3/2008 |
| GB | 2028825 | 3/1980 |
| WO | 2008137050 | 11/2008 |
| WO | 2009012955 | 1/2009 |
| WO | 2009059765 | 5/2009 |
| WO | 2010118023 | 10/2010 |

OTHER PUBLICATIONS

Search Report for PCT/US2010/030092 mailed Jul. 20, 2010; 5 pages.
Written Opinion for PCT/US2010/030092 mailed Jul. 20, 2010; 11 pages.
XP-002460202; Bittler Dieter et al: "Synthesis of a new highly effective aldosterone antagonist (spirorenone)/Synthese von Spirorenon, einem neuen stark wirksamen Aldosteron-Antagonisten"; vol. 94, No. 9, pp. 718-719, Jan. 1, 1982.
XP-002591025; Faraj et al: "Synthesis of New Steroidal 11-Beta-Substituted Spirolactones" Journal of the Chemical Society, Perkin Transactions 1., 1990, pp. 3045-3048.
XP-002591024; Creger: "Metalated Carboxylic Acids. IV. Reactions of Metalated Carboxylic Acids with Epoxides. Substituted Steroidal gamma-Lactones from Spiro Beta-Epoxides", Journal of Organic Chemistry, vol. 37, No. 12, pp. 1907-1918, 1972.
XP-002510283; Sam et al: "Steroidal Sprio-.gamma.-lactones that inhibit 17.beta.-hydroxysteroid dehydrogenase activity in human placental mircosomes", Journal of Medicinal Chemistry, American Chemical Society, vol. 38, No. 22, Jan. 1, 1995, pp. 4518-4528.

*Primary Examiner* — Brenda Coleman
(74) *Attorney, Agent, or Firm* — Meyertons, Hood, Kivlin, Kowert & Goetzel, P.C.; Eric B. Meyertons

(57) ABSTRACT

Described herein are methods of making drospirenone. Also described are intermediate compounds that may be used to synthesis drospirenone.

19 Claims, 5 Drawing Sheets

METHODS FOR THE PREPARATION OF DROSPIRENONE

PRIORITY CLAIM

This application claims the benefit of U.S. Provisional Application No. 61/168,261 filed on Apr. 10, 2009 and U.S. Provisional Application No. 61/240,413 filed on Sep. 8, 2009.

BACKGROUND OF THE INVENTION

1. Field of the Invention

The present invention generally relates to processes for the synthesis of drospirenone.

2. Description of the Relevant Art

Drospirenone is a synthetic steroid with progestin, anti-mineral corticoid and anti androgen activity. Drospirenone is currently being used as a synthetic progestin in oral contraceptive formulations. A regioselective synthesis for drospirenone has been described (see e.g., Angew. Chem. 94, 1982, 718) that uses the 17 keto derivative (1) as a key intermediate.

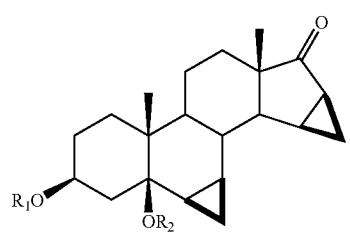

(1)

The synthesis of intermediate (1) and the transformation of intermediate (1) into drospirenone has been described in, for example, U.S. Published Patent Application Nos. 2009/0023914; 20080207575; 2008/0200668; 2008/0076915; 20070049747, and 20050192450; U.S. Pat. Nos. 6,933,395; 6,121,465, and 4,129,564, European Patent No. 0 075 189 and PCT Publication No. WO 2006/061309, all of which are incorporated herein by reference. Many of these routes introduce the required C3 side chain in the 17 position of intermediate (1). These conversions are usually carried out with carbanions, such as propargylalcohol, trimethylsulfoxonium iodide, or the use of the anion generated from a suitably protected derivative of 1-bromopropionaldehyde. After oxidation of the 3-hydroxy substituent to a 3-keto group, and the oxidative formation of the 17-spirolactone, the 3-keto-5-hydroxy-17-spirolactone is transformed via acid catalysis into drospireneone. If the oxidation is performed under acidic conditions at elevated temperatures, the oxidation and elimination can be run without isolation of the intermediate products.

Most of these procedures rely on the acid-catalyzed elimination of the 5-hydroxy group in the last step of the synthesis. It has been documented that 15,16-methylene-17-spirolactones are prone to undergo rearrangement to generate the inverted 17-spirolactone under mild acidic conditions (see, for example, Tetrahedron Letters, Vol. 27, No 45, 5463-5466) in considerable amounts. This isomer has very similar physical chemical properties, and typically requires chromatographic separation or repeated fractional recrystallizations to purify the product. This isomerization can make these approaches less desirable from an economical point of view.

For the above given arguments, a process that avoids the acidic treatment of intermediates containing the 15,16-methylene-17-spirolactone could offer a significant advantage because of the avoidance of the generation of the undesired 17-spirolactone isomer.

SUMMARY OF THE INVENTION

In one embodiment, a method of making drospirenone includes:

reacting the intermediate (1) with a propargyl alcohol anion, as depicted in the reaction (I) to yield intermediate (2), where each $R^1$, $R^2$ is independently H, $Si(R^5)_3$, $C(R^6)_2(OR^5)$ or $CR^6(OR^5)_2$; Z is $CH_2OR^3$, CN, or $CO_2R^4$; where each $R^3$ is independently alkyl, $Si(R^5)_3$, or $CH(OR^5)_2$, phenyl, or benzyl; each $R^4$ and $R^5$ is independently hydrogen, alkyl, phenyl, benzyl, or an alkali metal and each $R^6$ is independently alkyl or hydrogen;

(I)

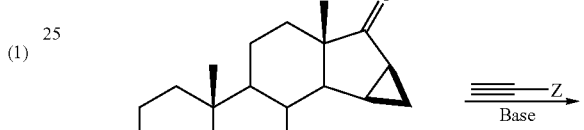

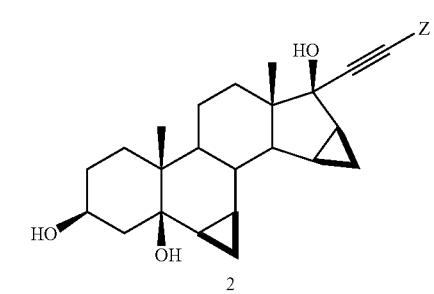

reducing the alkyne functionality of intermediate (2) to form intermediate (3), as depicted in reaction (II);

(II)

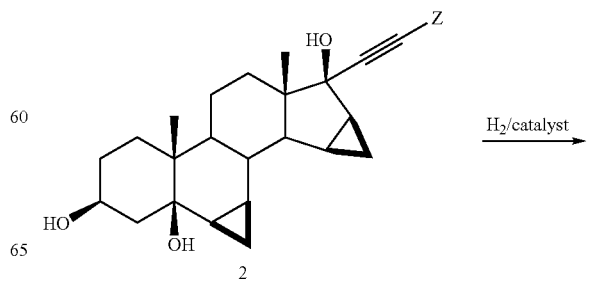

-continued

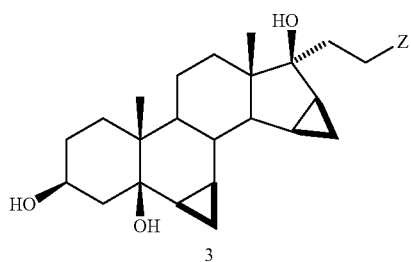

oxidizing intermediate (3) to form intermediate (4), as depicted in reaction (III);

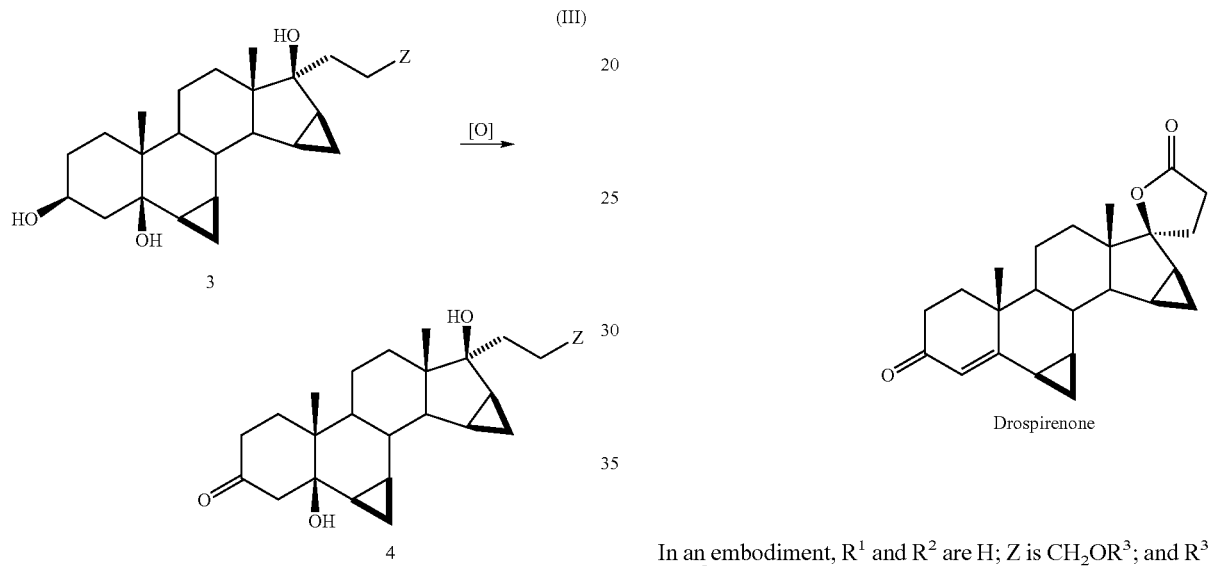

treating intermediate (4) with a base to produce intermediate (5), as depicted in reaction (IV); and

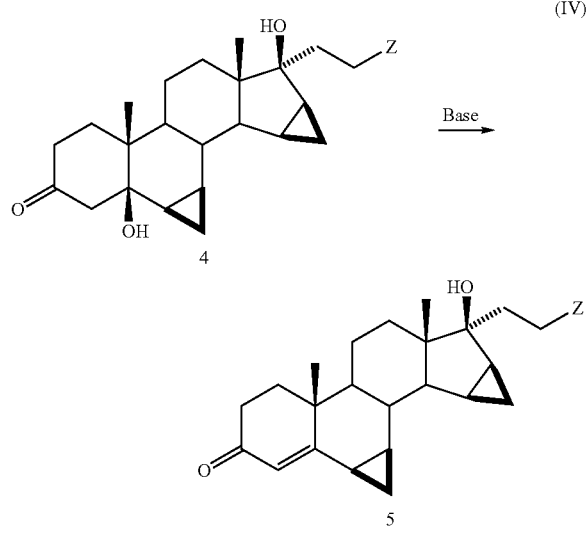

converting the intermediate (5) to drospirenone by forming the spirolactone substitutent, as depicted in reaction (V).

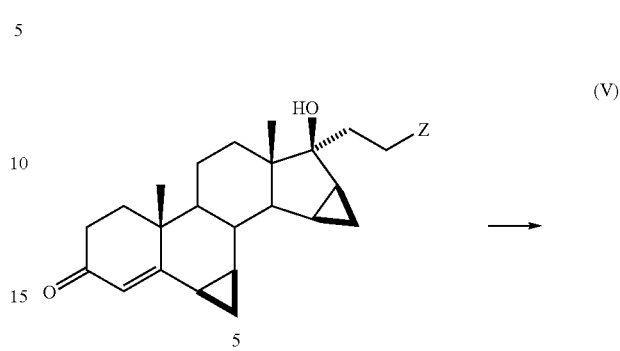

In an embodiment, $R^1$ and $R^2$ are H; Z is $CH_2OR^3$; and $R^3$ is $Si(R^5)_3$. In reaction (I) the propargyl alcohol anion may be generated by the reaction of $HC{\equiv}CCH_2OR^3$ with potassium t-butoxide, wherein $R^3$ is tert-butyldimethyl silyl. Reaction (III) may be performed using a chromium based oxidation. The elimination reaction (IV) may be performed using an alkali metal alkyloxide. The conversion of intermediate (5) to drospirenone is performed using a chromium based oxidation.

In an embodiment, $R^1$ and $R^2$ are H; Z is $CH_2CO_2R^4$; and $R^4$ is alkyl. In reaction (I) the propargyl alcohol anion may be generated by the reaction of $HC{\equiv}CCH_2CO_2R$ with lithium hexamethyldisilylamide. The oxidation reaction (III) may be performed using 2,2,6,6-tetramethylpiperidine-1-oxyl or a derivative thereof. The elimination reaction (IV) may be performed using an alcoholic alkali hydroxide. The conversion of intermediate (5) to drospirenone may be performed under acidic conditions (e.g., using an organic acid). In either embodiment, reaction (II) may be performed using Pd in the presence of hydrogen.

In an alternate embodiment, a method of making drospirenone comprising:

reacting the intermediate (1) with a propargyl alcohol, as depicted in the reaction (V) to yield intermediate (2), where each $R^1$, $R^2$ is independently H, $Si(R^5)_3$, $C(R^6)_2$ $(OR^5)$ or $CR^6(OR^5)_2$; Z is CN or $CO_2R^4$; where each $R^3$ is independently alkyl, $Si(R^5)_3$, or $CH(OR^5)_2$, phenyl, or benzyl; each $R^4$ and $R^5$ is independently hydrogen, alkyl, phenyl, benzyl, or an alkali metal and each $R^6$ is independently alkyl or hydrogen;

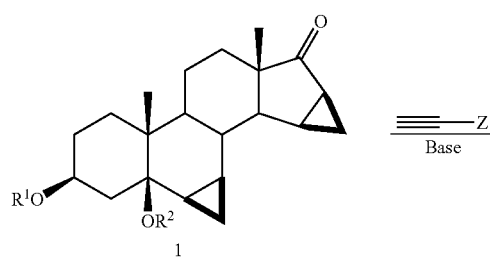

(V)

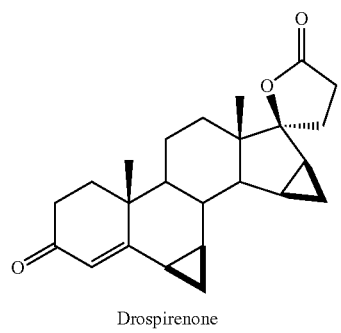

Drospirenone

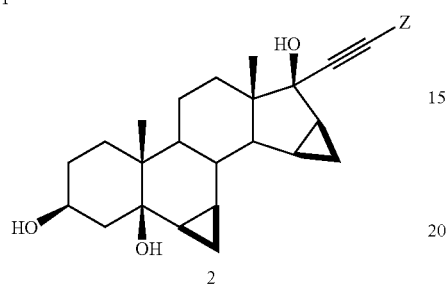

oxidizing intermediate (2) to form intermediate (9), as depicted in reaction (VI);

In an embodiment, $R^1$ and $R^2$ are H; Z is $CH_2CO_2R^4$; and $R^4$ is alkyl. In reaction (V) the propargyl alcohol anion may be generated by the reaction of $HC{\equiv}CCH_2CO_2R$ with lithium hexamethyldisilylamide. The oxidation of reaction (VI) may be performed using 2,2,6,6-tetramethylpiperidine-1-oxyl or a derivative thereof. The conversion of intermediate (9) to drospirenone, in one embodiment, includes:

reducing the alkyne functionality of intermediate (9) to form intermediate (8), as depicted in reaction (VIII); and

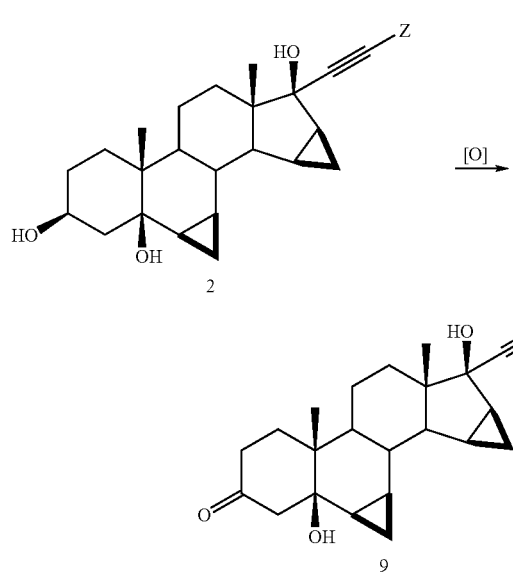

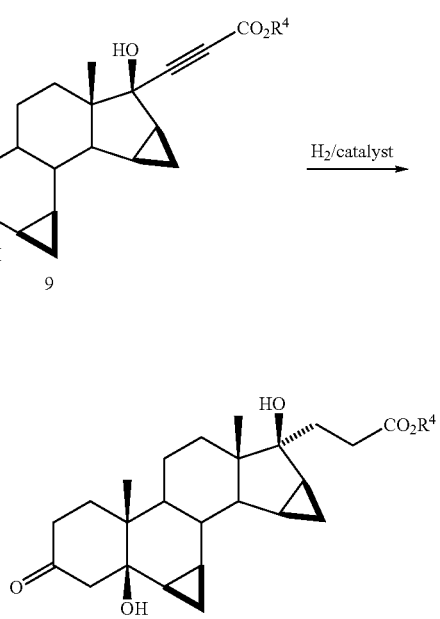

converting the intermediate (9) to drospirenone as depicted in reaction (VII).

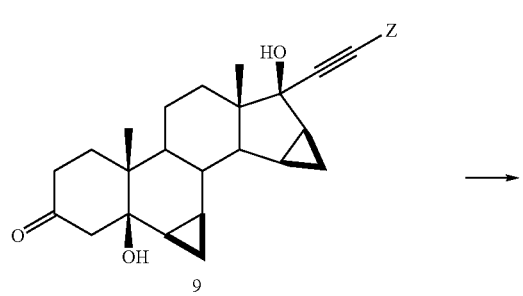

treating intermediate (8) with an aqueous base followed by an aqueous acid to form drospirenone.

In an embodiment, reaction (VIII) is performed using Pd in the presence of hydrogen. The conversion of intermediate (9) to drospirenone, in an embodiment, includes:

treating intermediate (9) with an aqueous acid to produce intermediate (10), as depicted in reaction (IX); and

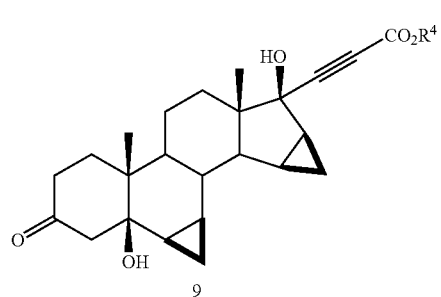
(IX)

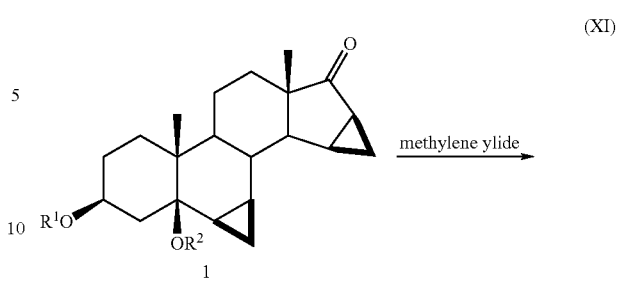
(XI)

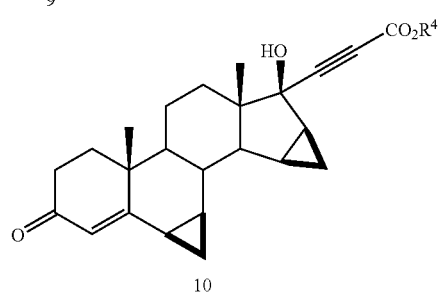
(X)

reducing the alkyne functionality of intermediate (10) to form intermediate (11), as depicted in reaction (X); and reacting the intermediate (12) with a carbanion as depicted in the reaction (XII) to yield intermediate

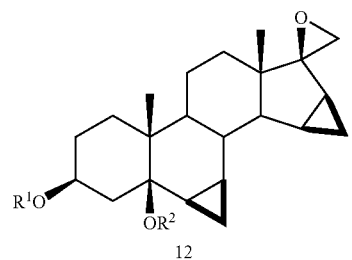
(XII)

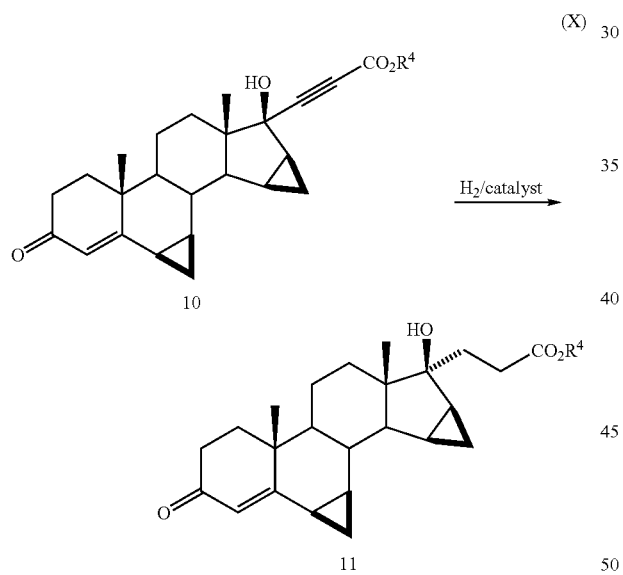

treating intermediate (11) with an aqueous base followed by an aqueous acid to form drospirenone.

Reaction (X) is performed using a metal catalyst, including, but not limited to, Rh, Raney Nickel, Ir, and Pd in the presence of hydrogen.

In an alternate embodiment, a method of making drospirenone includes:

reacting the intermediate (1) with a methylene ylide, as depicted in the reaction (XI) to yield intermediate (12), where each $R^1$, $R^2$ is independently H, $Si(R^5)_3$, $C(R^6)_2(OR^5)$ or $CR^6(OR^5)_2$; Z is $CH_2OR^3$, CN, or $CO_2R^4$; where each $R^3$ is independently alkyl, $Si(R^5)_3$, or $CH(OR^5)_2$, phenyl, or benzyl; each $R^4$ and $R^5$ is independently hydrogen, alkyl, phenyl, benzyl, or an alkali metal and each $R^6$ is independently alkyl or hydrogen;

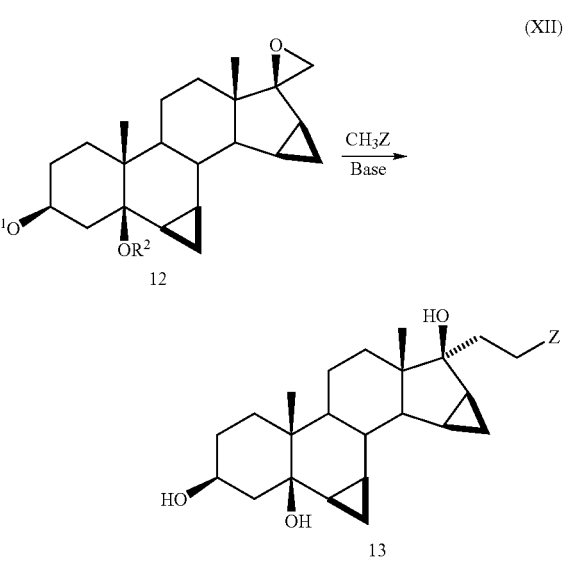

oxidizing intermediate (L) to form intermediate (14), as depicted in reaction (XIII);

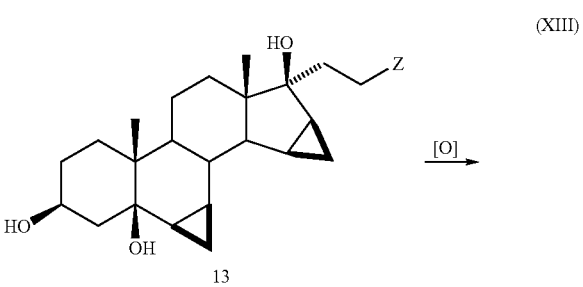
(XIII)

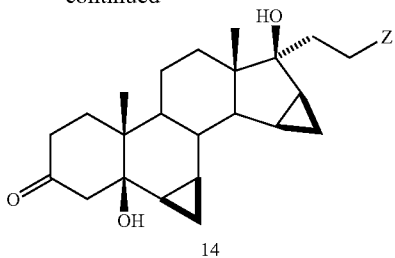

14 converting the intermediate (14) to drospirenone as depicted in reaction (XIV).

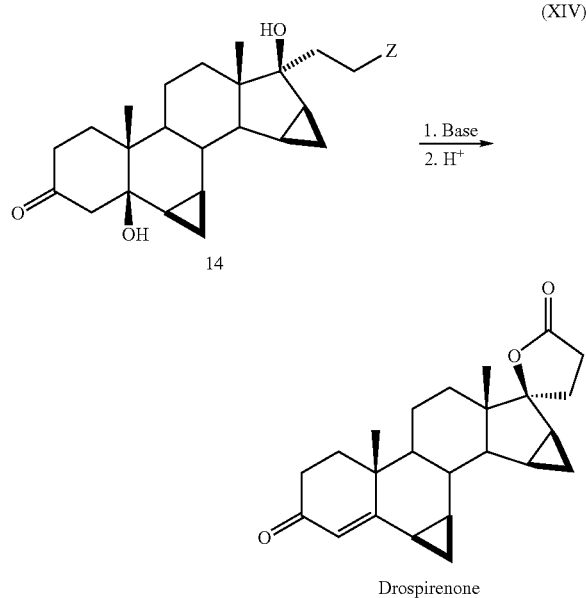

In an embodiment, the methylene ylide is a sulfur ylide. In an embodiment, Z is CN, and $R^1$ and $R^2$ are $C(R^6)_2(OR^5)$. The oxidation of reaction (XIII) is performed using a chromium based oxidation. The conversion of intermediate (14) to drospirenone may be performed by treating intermediate (14) with an aqueous base followed by an aqueous acid to form drospirenone.

In an embodiment, drospirenone may be synthesized from any compound having the structure 15:

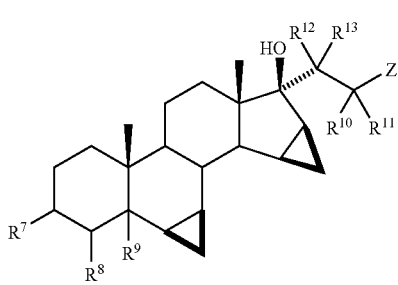

where Z is CN or $CO_2R^4$; $R^7$ is —$OR^1$ or =O; $R^8$ is H and $R^9$ is —$OR^2$ or $R^1$ and $R^2$ together form a double bond; $R^{10}$, $R^{11}$, $R^{12}$, and $R^{13}$ are H or $R^{10}$, $R^{11}$, $R^{12}$, and $R^{13}$ together form a triple bond; where each $R^1$ and $R^2$ is independently H, Si$(R^5)_3$, $C(R^6)_2(OR^5)$ or $CR^6(OR^5)_2$; where each $R^4$ and $R^5$ is independently hydrogen, alkyl, phenyl, benzyl, or an alkali metal; and each $R^6$ is independently alkyl or hydrogen.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
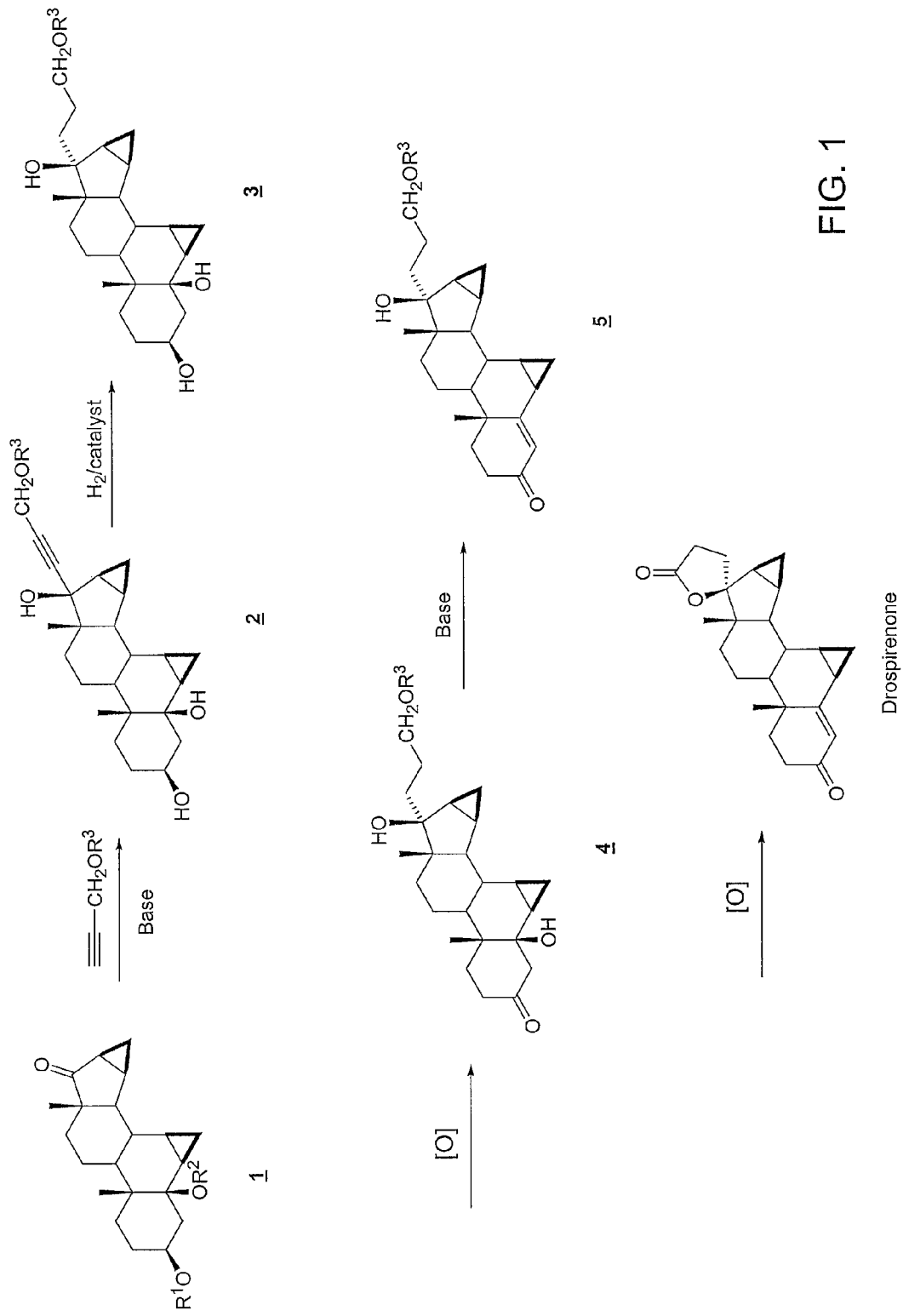
FIGS. 1-5 depict alternate reaction schemes for the synthesis of drospirenone.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

In one embodiment, drospirenone may be synthesized according to the scheme depicted in FIG. 1. FIG. 1 depicts a propargyl alcohol anion addition to the 17-keto substituent of the intermediate (1). $R^1$ and $R^2$ of intermediate (1) may be H, Si$(R^5)_3$, $C(R^6)_2(OR^5)$ or $CR^6(OR^5)_2$ where each $R^5$ is independently alkyl, phenyl, or benzyl, and each $R^6$ is independently alkyl or hydrogen. The propargyl alcohol anion has the structure: $^-C{\equiv}CCH_2OR^3$; where $R^3$ is independently alkyl, Si$(R^5)_3$, or CH$(OR^5)_2$, phenyl, or benzyl; and each $R^5$ is independently alkyl, phenyl, or benzyl. A lithium or potassium anion of the propargyl alcohol may be generated in situ using know methods as described in U.S. Published Patent Application Nos.: 2009/0023914; 20080207575; and 20050192450; and U.S. Pat. Nos. 6,933,395 and 6,121,465, all of which are incorporated herein by reference. Reaction of the propargyl alcohol anion with intermediate (1) generates the 17-hydroxy addition product (2).

The 17-hydroxy addition product (2) may be hydrogenated in the presence of a suitable catalyst (e.g., Pd, Pt, Rh, Ru, Ir, Ni, and Raney Nickel) in the presence of hydrogen to give the saturated intermediate (3). Examples of suitable catalysts include, but are not limited to Pd/C and rhodium phosphine catalysts.

The resulting hydrogenated intermediate (3) may be treated with an oxidant to oxidize the 3-hydroxy substituent without effecting formation of the 17-spirolactone. Suitable oxidants include, but are not limited to chromium based oxidants ($CrO_3$/pyridine, Jones reagent, pyridinium dichromate (PDC), pyridinium chlorochromate (PCC), etc.), IBX, $KMnO_4$, $MnO_2$, $RuO_4$ and 2,2,6,6-Tetramethylpiperidine-1-oxyl (TEMPO) or derivatives of TEMPO (e.g., 4-hydroxy-TEMPO, 4-acetamido-TEMPO, 4-methoxy-TEMPO, 4-benzyl-TEMPO, and polymer-supported TEMPO). Further details regarding TEMPO oxidations of steroidal compounds is described in U.S. Patent No. 2007/0049747 to Seilz et al., which is incorporated herein by reference. Oxidation of the 3-hydroxy substituent leads to the 3-keto-5-hydroxy intermediate (4) depicted in FIG. 1.

The resulting 3-keto-5-hydroxy inteimmediate (4) may be dehydrated by acid or base catalyzed dehydration of the 5-hydroxy substituent to give the 3-keto-4-ene intermediate (5). Base catalyzed elimination my be effected by the treatment with an alkali metal alkyloxide (e.g, sodium methoxide). Other bases include tertiary amines (triethyamine, pyridine, etc.), alkali metal hydroxides in water and/or alcohol, or carbonate bases (e.g., $K_2CO_3$).

Treatment of the 3-keto-4-ene intermediate (5) with a suitable oxidant yields drospirenone. Suitable oxidants include, but are not limited to chromium based oxidants ($CrO_3$/pyridine, Jones reagent, pyridinium dichromate (PDC), pyridinium chlorochromate (PCC), etc.), IBX, $KMnO_4$, $MnO_2$, $RuO_4$ and 2,2,6,6-Tetramethylpiperidine-1-oxyl (TEMPO) or derivatives of TEMPO (e.g., 4-hydroxy-TEMPO, 4-acetamido-TEMPO, 4-methoxy-TEMPO, 4-benzyl-TEMPO, and polymer-supported TEMPO). Further details regarding TEMPO oxidations of steroidal compounds is described in U.S. Patent No. 2007/0049747 to Seilz et al., which is incorporated herein by reference. An advantage of the synthesis depicted in FIG. 1 is that the propargyl group acts as a protecting group to inhibit formation of the 17-spirolactone substituent during oxidation of the 3-hydroxy substituent. After the oxidation of the 3-hydroxy substituent is accomplished, the propargyl group may be reduced to its saturated form. The base catalyzed elimination of the 5-hydroxy group to form the 3-keto-4-ene portion of drospirenone may be performed without any concern for isomerization, since the spirolactone cannot be formed under the basic elimination conditions until the propargyl alcohol is oxidized.

Figure 2:
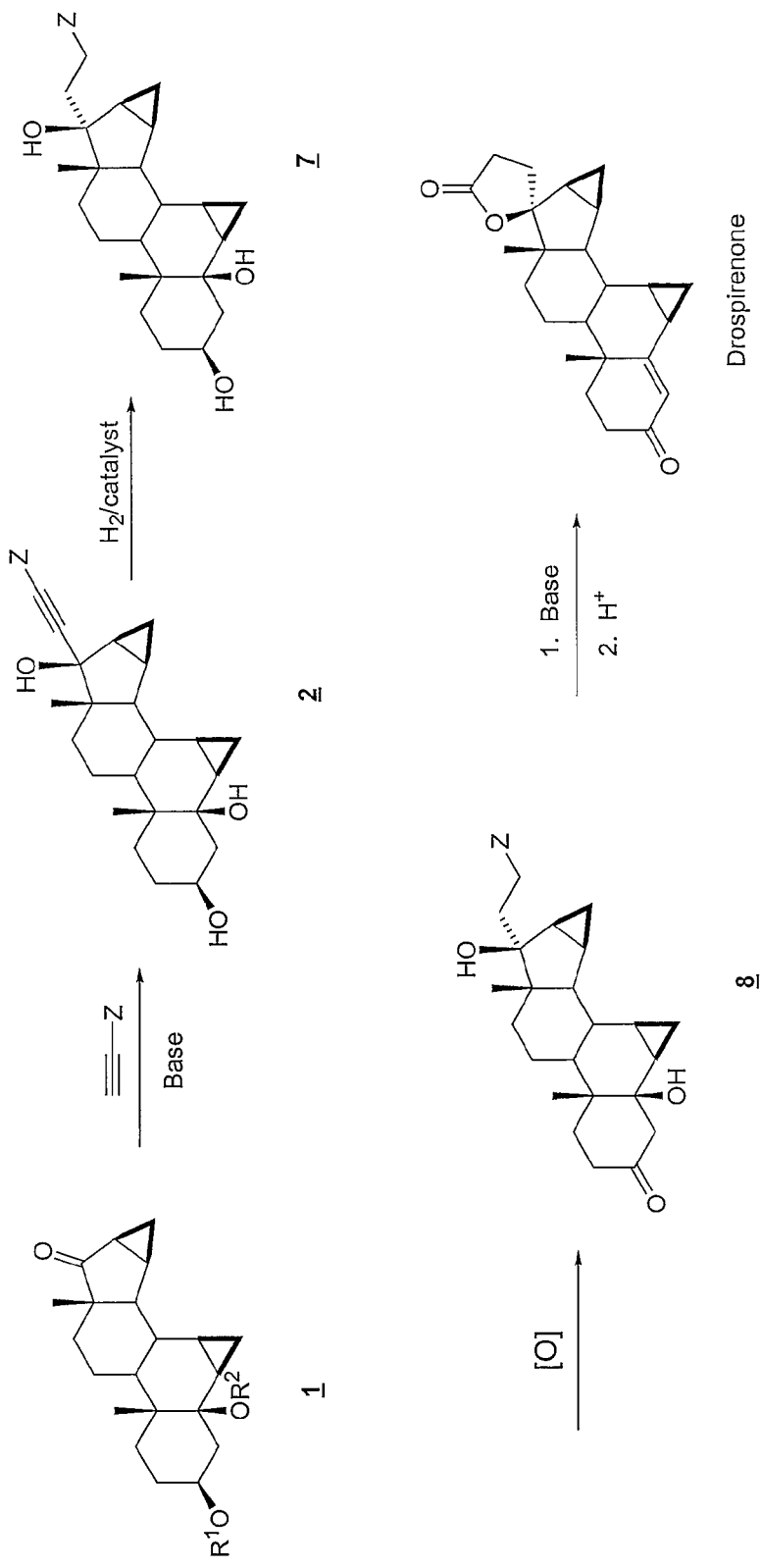

Another example of a synthesis of drospirenone is depicted in FIG. 2. FIG. 2 depicts a propargyl alcohol anion addition to the 17-keto substituent of the intermediate (1). $R^1$ and $R^2$ of intermediate (1) may be H, $Si(R^5)_3$, $C(R^6)_2(OR^5)$ or $CR^6(OR^5)_2$ where each $R^5$ is independently alkyl, phenyl, or benzyl, and each $R^6$ is independently alkyl or hydrogen. The propargyl alcohol anion has the structure: $^-C\equiv CZ$, where Z is CN or $CO_2R^4$; where $R^3$ is independently alkyl, $Si(R^5)_3$, or $CH(OR^5)_2$, phenyl, or benzyl; and each $R^4$ and $R^5$ is independently hydrogen, alkyl, phenyl, benzyl, or an alkali metal. A lithium or potassium anion of the propargyl alcohol may be generated in situ using know methods as described above, all of which are incorporated herein by reference. Reaction of the propargyl alcohol anion with intermediate (1) generates the 17-hydroxy addition product (2).

The 17-hydroxy addition product (2) may be hydrogenated in the presence of a suitable catalyst (e.g., Pd, Pt, Rh, Ru, Ir, Ni, and Raney Nickel) to give the saturated intermediate (2). Examples of suitable catalysts include, but are not limited to Pd/C and rhodium phosphine catalysts.

The resulting hydrogenated intermediate (7) may be treated with an oxidant to oxidize the 3-hydroxy substituent without effecting formation of the 17-spirolactone. Suitable oxidants include, but are not limited to chromium based oxidants ($CrO_3$/pyridine, Jones reagent, pyridinium dichromate (PDC), pyridinium chlorochromate (PCC), etc.), IBX, $KMnO_4$, $MnO_2$, $RuO_4$ and 2,2,6,6-Tetramethylpiperidine-1-oxyl (TEMPO) or derivatives of TEMPO (e.g., 4-hydroxy-TEMPO, 4-acetamido-TEMPO, 4-methoxy-TEMPO, 4-benzyl-TEMPO, and polymer-supported TEMPO). Further details regarding TEMPO oxidations of steroidal compounds is described in U.S. Patent No. 2007/0049747 to Seilz et al., which is incorporated herein by reference. Oxidation of the 3-hydroxy substituent leads to the 3-keto-5-hydroxy intermediate (8) depicted in FIG. 2.

The resulting 3-keto-5-hydroxy intermediate (8) may be converted to drospirenone in a two step process. In the first step, treatment with an aqueous base effects both dehydration of the 5 hydroxy substituent and hydrolysis of the —Z group (either —CN or $CO_2R^4$). Suitable bases include alkali metal hydroxides in water and/or a water/alcohol mixture, or carbonate bases (e.g., $K_2CO_3$) in water or a water/alcohol mixture. Acidification of the resulting intermediate 3-keto-4-ene using an acid (e.g., an organic acid such as acetic acid) results in drospirenone.

Figure 3:
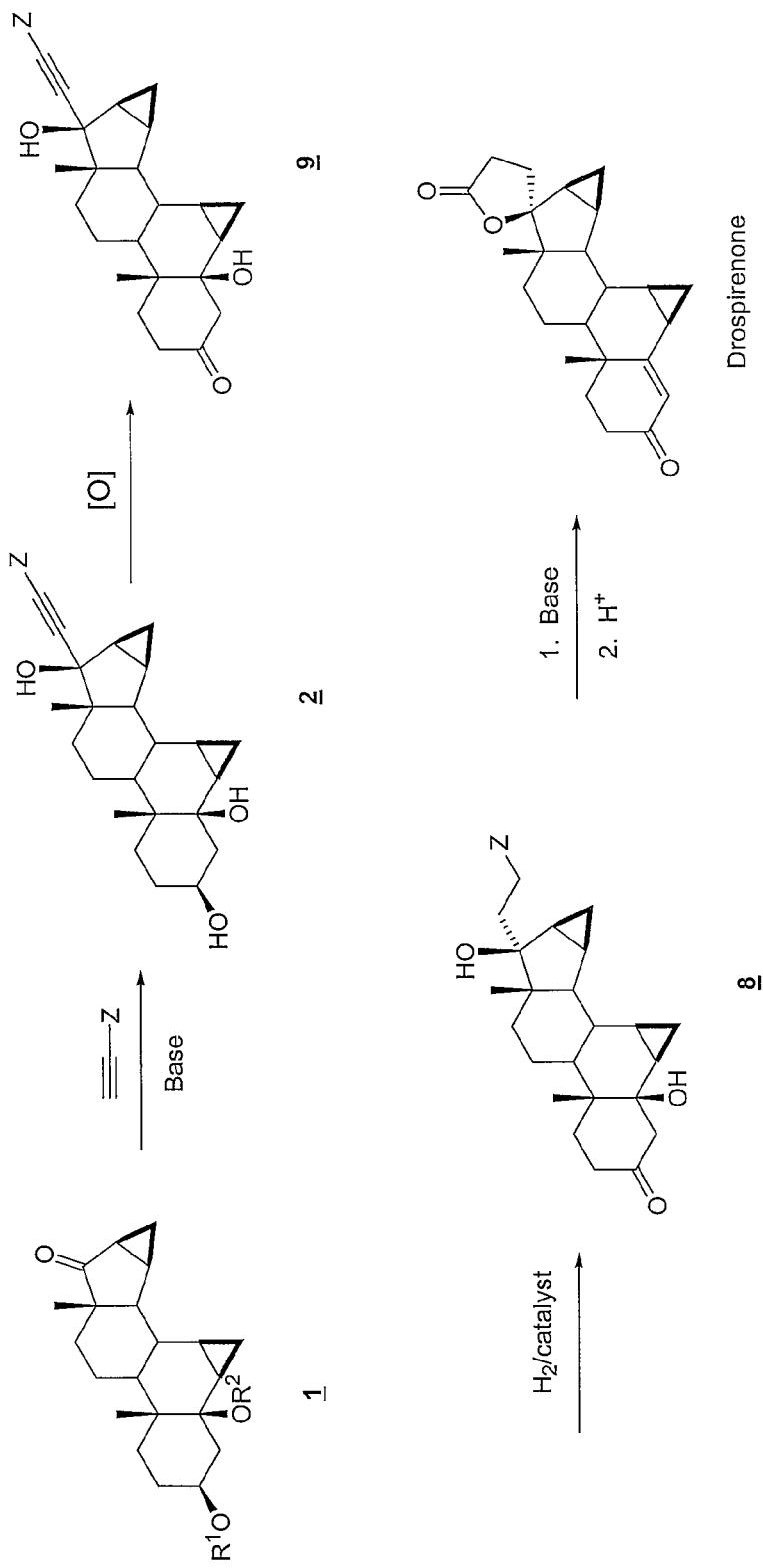

Another example of a synthesis of drospirenone is depicted in FIG. 3. FIG. 3 depicts a propargyl alcohol anion addition to the 17-keto substituent of the intermediate (1). $R^1$ and $R^2$ of intermediate (1) may be H, $Si(R^5)_3$, $C(R^6)_2(OR^5)$ or $CR^6(OR^5)_2$ where each $R^5$ is independently alkyl, phenyl, or benzyl, and each $R^6$ is independently alkyl or hydrogen. The propargyl alcohol anion has the structure: $^-C\equiv CZ$, where Z is CN or $CO_2R^4$; where $R^3$ is independently alkyl, $Si(R^5)_3$, or $CH(OR^5)_2$, phenyl, or benzyl; and each $R^4$ and $R^5$ is independently hydrogen, alkyl, phenyl, benzyl, or an alkali metal. A lithium or potassium anion of the propargyl alcohol may be generated in situ using know methods as described above, all of which are incorporated herein by reference. Reaction of the propargyl alcohol anion with intermediate (1) generates the 17-hydroxy addition product (2).

The resulting addition product (2) may be treated with an oxidant to oxidize the 3-hydroxy substituent without effecting formation of the 17-spirolactone. Suitable oxidants include, but are not limited to chromium based oxidants ($CrO_3$/pyridine, Jones reagent, pyridinium dichromate (PDC), pyridinium chlorochromate (PCC), etc.), IBX, $KMnO_4$, $MnO_2$, $RuO_4$ and 2,2,6,6-Tetramethylpiperidine-1-oxyl (TEMPO) or derivatives of TEMPO (e.g., 4-hydroxy-TEMPO, 4-acetamido-TEMPO, 4-methoxy-TEMPO, 4-benzyl-TEMPO, and polymer-supported TEMPO). Further details regarding TEMPO oxidations of steroidal compounds is described in U.S. Patent No. 2007/0049747 to Seilz et al., which is incorporated herein by reference. Oxidation of the 3-hydroxy substituent leads to the 3-keto-5-hydroxy intermediate (2) depicted in FIG. 2.

The 3-keto-5-hydroxy intermediate (9) may be hydrogenated in the presence of a suitable catalyst (e.g., Pd, Pt, Rh, Ru, Ir, Ni, and Raney Nickel) to give the saturated intermediate (8). Examples of suitable catalysts include, but are not limited to Pd/C and rhodium phosphine catalysts.

The resulting saturated intermediate (8) may be converted to drospirenone in a two step process. In the first step, treatment with an aqueous base effects both dehydration of the 5 hydroxy substituent and hydrolysis of the —Z group (either —CN or $CO_2R^4$). Suitable bases include alkali metal hydroxides in water and/or a water/alcohol mixture, or carbonate bases (e.g., $K_2CO_3$) in water or a water/alcohol mixture. Acidification of the resulting intermediate 3-keto-4-ene using an acid (e.g., an organic acid such as acetic acid) results in drospirenone.

Figure 4:
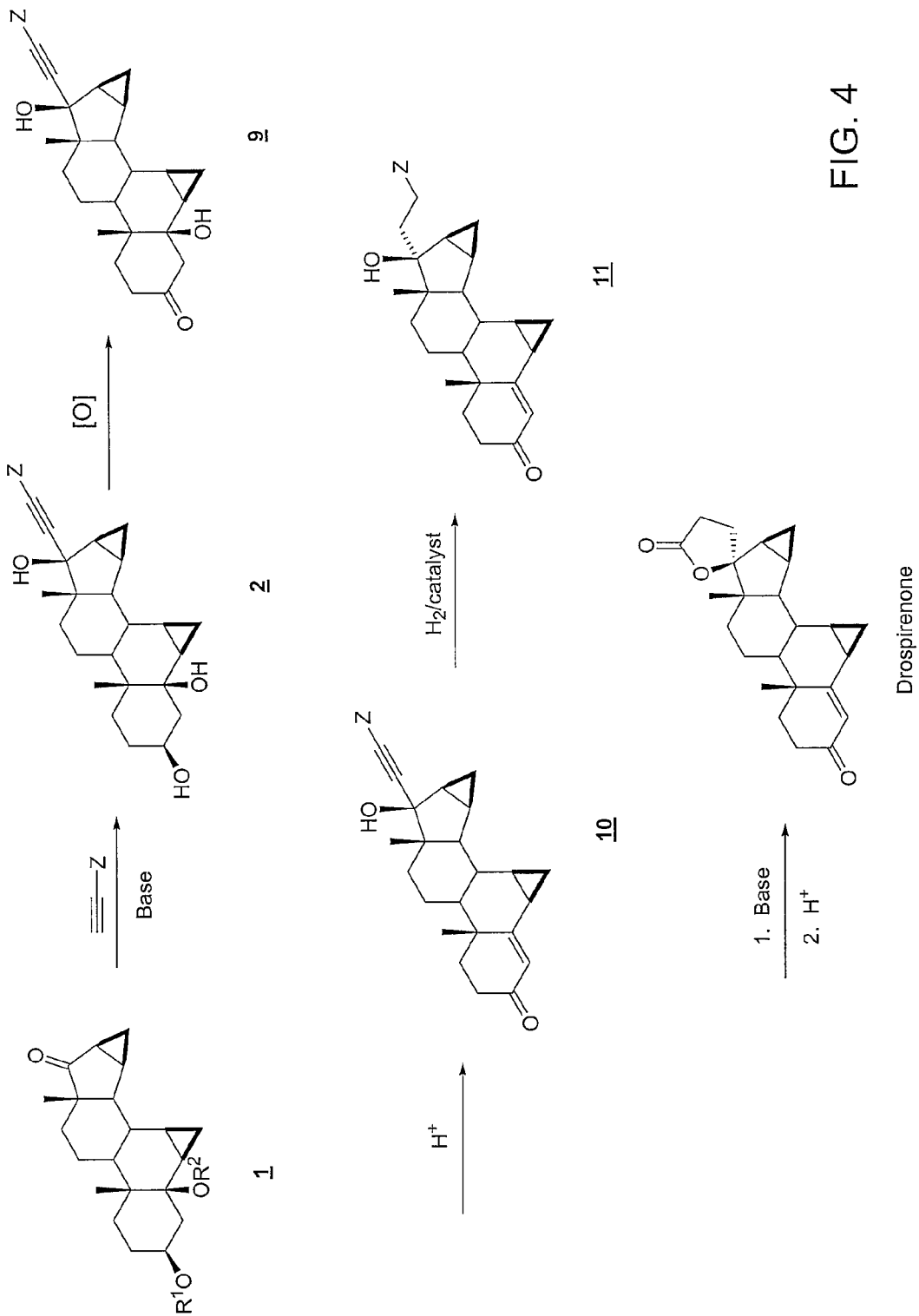

Another example of a synthesis of drospirenone is depicted in FIG. 4. FIG. 4 depicts a propargyl alcohol anion addition to the 17-keto substituent of the intermediate (1). $R^1$ and $R^2$ of intermediate (1) may be H, $Si(R^5)_3$, $C(R^6)_2(OR^5)$ or $CR^6(OR^5)_2$ where each $R^5$ is independently alkyl, phenyl, or benzyl, and each $R^6$ is independently alkyl or hydrogen. The propargyl alcohol anion has the structure: $^-C\equiv CZ$, where Z is CN or $CO_2R^4$; where $R^3$ is independently alkyl, $Si(R^5)_3$, or $CH(OR^5)_2$, phenyl, or benzyl; and each $R^4$ and $R^5$ is independently hydrogen, alkyl, phenyl, benzyl, or an alkali metal. A lithium or potassium anion of the propargyl alcohol may be generated in situ using know methods as described above, all of which are incorporated herein by reference. Reaction of the propargyl alcohol anion with intermediate (1) generates the 17-hydroxy addition product (2).

The resulting addition product (2) may be treated with an oxidant to oxidize the 3-hydroxy substituent without effecting formation of the 17-spirolactone. Suitable oxidants include, but are not limited to chromium based oxidants (CrO₃/pyridine, Jones reagent, pyridinium dichromate (PDC), pyridinium chlorochromate (PCC), etc.), IBX, KMnO₄, MnO₂, RuO₄ and 2,2,6,6-Tetramethylpiperidine-1-oxyl (TEMPO) or derivatives of TEMPO (e.g., 4-hydroxy-TEMPO, 4-acetamido-TEMPO, 4-methoxy-TEMPO, 4-benzyl-TEMPO, and polymer-supported TEMPO). Further details regarding TEMPO oxidations of steroidal compounds is described in U.S. Patent No. 2007/0049747 to Seilz et al., which is incorporated herein by reference. Oxidation of the 3-hydroxy substituent leads to the 3-keto-5-hydroxy intermediate (9) depicted in FIG. 2.

The resulting 3-keto-5-hydroxy intermediate (9) may be dehydrated by acid or base catalyzed dehydration of the 5-hydroxy substituent to give the 3-keto-4-ene intermediate (10). Base catalyzed elimination may be effected by the treatment with an alkali metal alkyloxide (e.g, sodium methoxide). Other bases include tertiary amines (triethylamine, pyridine, etc.), alkali metal hydroxides in water and/or alcohol, or carbonate bases (e.g., K₂CO₃). Acid catalyzed elimination may be effected by the use of a mineral acid in a water/alcohol mixture. For example, acid catalyzed dehydration may be performed using a mixture of sulfuric acid in methanol.

The 3-keto-5-hydroxy intermediate (10) may be hydrogenated in the presence of a a suitable catalyst (e.g., Pd, Pt, Rh, Ru, Ir, Ni, and Raney Nickel) to give the saturated intermediate (11). Examples of suitable catalysts include, but are not limited to Pd/C and rhodium phosphine catalysts.

The resulting saturated intermediate (11) may be converted to drospirenone in a two step process. In the first step, treatment with an aqueous base effects both dehydration of the 5 hydroxy substituent and hydrolysis of the —Z group (either —CN or CO₂R⁴). Suitable bases include alkali metal hydroxides in water and/or a water/alcohol mixture, or carbonate bases (e.g., K₂CO₃) in water or a water/alcohol mixture. Acidification of the resulting intermediate 3-keto-4-ene using an acid (e.g., an organic acid such as acetic acid) results in drospirenone.

Figure 5:
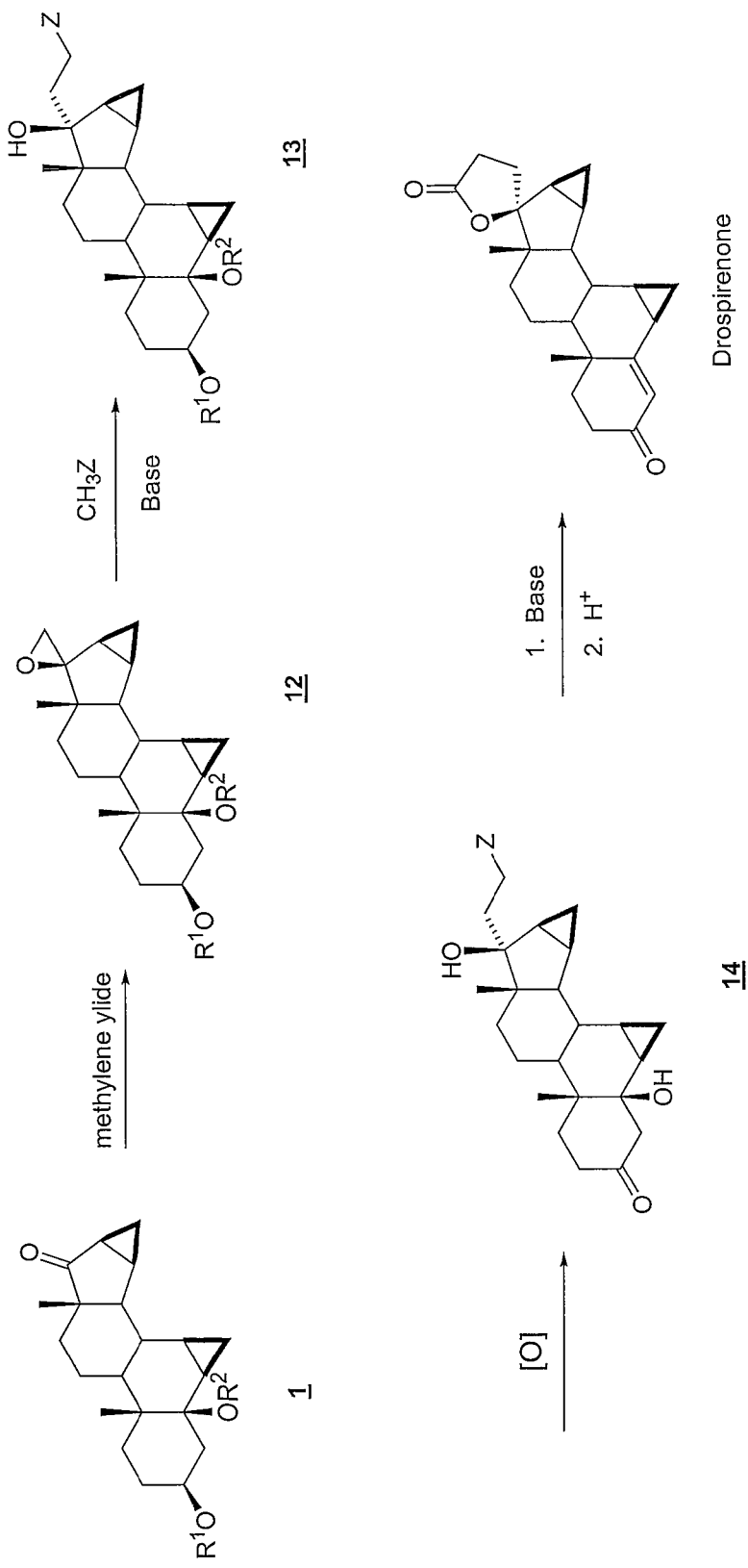

In an alternate embodiment, drospirenone may be synthesized via an oxirane. FIG. 5 depicts a synthesis in which intermediate (1) is converted to an oxirane by the use of a methylene ylide. R¹ and R² of intermediate (1) may be H, Si(R⁵)₃, C(R⁶)₂(OR⁵) or CR⁶(OR⁵)₂ where each R⁵ is independently alkyl, phenyl, or benzyl, and each R⁶ is independently alkyl or hydrogen.

Methylene ylides that be used include sulfur ylides and selenium ylides. Sulfur ylides include, but are not limited to dimethyloxosulfonium methylide, (CH₃)₂SOCH₂, also known as the Corey-Chaykovsky reagent ("CCR"), dimethylsulfonium methylide, and (CH₃)₂SCH₂. CCR may be obtained from trimethyl sulfoxonium iodide, obtained by reaction of DMSO and methyl iodide, reacted with a strong base such as sodium hydride to generate CCR in situ. Selenium ylides include, but are not limited, PhSeCH₂ and MeSeCH₂.

The resulting oxirane is reacted with a carbanion having the structure ⁻CH—Z, where Z is CN or CO₂R⁴; where R⁴ is hydrogen, alkyl, phenyl, benzyl, or an alkali metal. A lithium or potassium anion of may be generated in situ using know methods. Reaction of the carbanion with intermediate (12) generates the 17-hydroxy addition product (12).

The resulting addition product (13) may be treated with an oxidant to oxidize the 3-hydroxy substituent without effecting formation of the 17-spirolactone. Suitable oxidants include, but are not limited to chromium based oxidants (CrO₃/pyridine, Jones reagent, pyridinium dichromate (PDC), pyridinium chlorochromate (PCC), etc.), IBX, KMnO₄, MnO₂, RuO₄ and 2,2,6,6-Tetramethylpiperidine-1-oxyl (TEMPO) or derivatives of TEMPO (e.g., 4-hydroxy-TEMPO, 4-acetamido-TEMPO, 4-methoxy-TEMPO, 4-benzyl-TEMPO, and polymer-supported TEMPO). Further details regarding TEMPO oxidations of steroidal compounds is described in U.S. Patent No. 2007/0049747 to Seilz et al., which is incorporated herein by reference. Oxidation of the 3-hydroxy substituent leads to the 3-keto-5-hydroxy intermediate (14) depicted in FIG. 2.

The resulting 3-keto-5-hydroxy intermediate (14) may be converted to drospirenone in a two step process. In the first step, treatment with an aqueous base effects both dehydration of the 5 hydroxy substituent and hydrolysis of the —Z group (either —CN or CO₂R⁴). Suitable bases include alkali metal hydroxides in water and/or a water/alcohol mixture, or carbonate bases (e.g., K₂CO₃) in water or a water/alcohol mixture. Acidification of the resulting intermediate 3-keto-4-ene using an acid (e.g., an organic acid such as acetic acid) results in drospirenone.

The methods described above have lead to a number of compounds that may be used to synthesis drospirenone. In an embodiment, drospirenone may be synthesized from any compound having the structure 15:

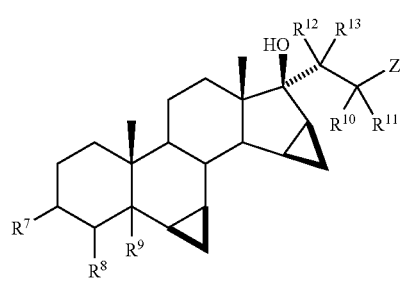

15 where Z is CN or CO₂R⁴;
R⁷ is —OR¹ or =O;
R⁸ is H and R⁹ is —OR² or R¹ and R² together form a double bond;
R¹⁰, R¹¹, R¹², and R¹³ are H or R¹⁰, R¹¹, R¹², and R¹³ together form a triple bond;
where each R¹ and R² is independently H, Si(R⁵)₃, C(R⁶)₂(OR⁵) or CR⁶(OR⁵)₂;
where each R⁴ and R⁵ is independently hydrogen, alkyl, phenyl, benzyl, or an alkali metal; and
each R⁶ is independently alkyl or hydrogen.

In an embodiment, the compound has the structure (16):

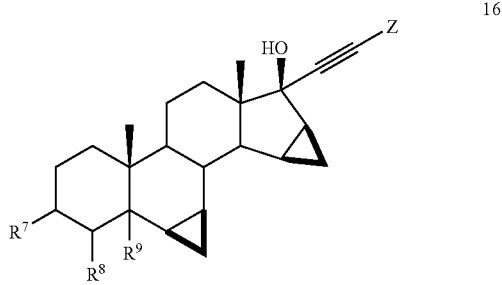

16 where Z is CN or CO$_2$R$^4$;

R$^7$ is —OR$^1$ or =O;

R$^8$ is H and R$^9$ is —OR$^2$ or R$^1$ and R$^2$ together form a double bond;

where each R$^1$ and R$^2$ is independently H, Si(R$^5$)$_3$, C(R$^6$)$_2$(OR$^5$) or CR$^6$(OR$^5$)$_2$;

where each R$^4$ and R$^5$ is independently hydrogen, alkyl, phenyl, benzyl, or an alkali metal; and each R$^6$ is independently alkyl or hydrogen.

In another embodiment, the compound has the structure (17):

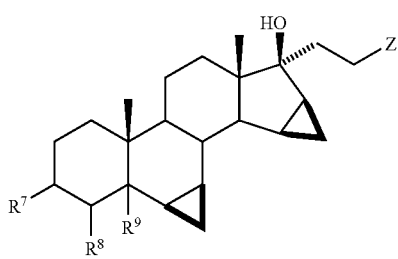

(17)

where Z is CN or CO$_2$R$^4$;

R$^7$ is —OR$^1$ or =O;

R$^8$ is H and R$^9$ is —OR$^2$ or R$^1$ and R$^2$ together form a double bond;

where each R$^1$ and R$^2$ is independently H, Si(R$^5$)$_3$, C(R$^6$)$_2$(OR$^5$) or CR$^6$(OR$^5$)$_2$;

where each R$^4$ and R$^5$ is independently hydrogen, alkyl, phenyl, benzyl, or an alkali metal; and each R$^6$ is independently alkyl or hydrogen.

Specific examples of compounds that may be used for the synthesis of drospirenone include the following:

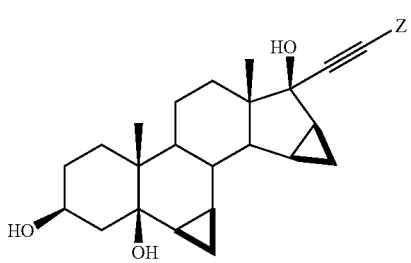

(18)

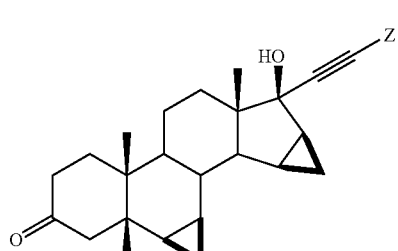

(19)

(20)

(21)

(22)

(23)

Where in each of compounds (18)-(23), Z is CN or CO$_2$R$^4$; and where R$^4$ is hydrogen, alkyl, phenyl, benzyl, or an alkali metal.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

FIG. 1

Experimental Example

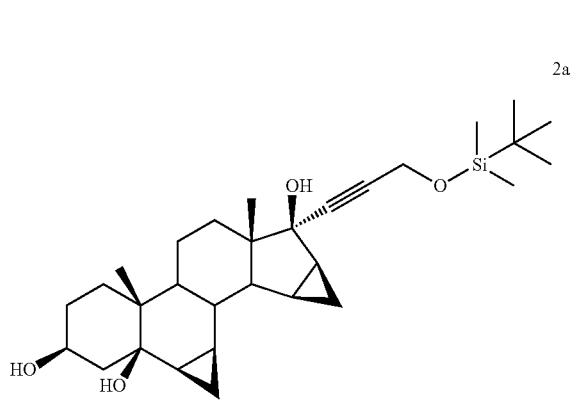

2a

A solution of compound (1) (5 g; 15.2 mmol) and tert-butyldimethyl (2-propynyloxy)silane (2.83 g, 16.7 mmol) in 75 ml of dry THF was added dropwise through an addition funnel to a precooled slurry of potassium tert-butoxide (8.49 g, 75.7 mmol) at −10 C. A thick white precipitate is formed during the addition and the resulting mixture was stirred for an hour at 0 C. TLC analysis (70% EtOAc/Hexanes) showed completion of the reaction and showed a less polar product. The reaction was quenched by the addition of ice water (100 ml) and neutralized by adding acetic acid (4.3 ml). The THF layer was separated and the aqueous layer was extracted with EtOAc (2×50 ml). The combined organic layers were washed with water (2×100 ml), brine (100 ml) and dried over anhydrous sodium sulfate. The solvent was removed under vacuum to afford compound (2a) (7.5 g, 99.2%) as a solid which was used in the next step without any purification.

NMR (CDCl$_3$) δ 0.139 (s, 6H, S$_1$—CH$_3$), 0.385 (m, 1H), 0.628 (m, 1H), 0.857 (s, 18-Me), 0.896 (s, 19-Me), 0.918 (s, 3H, Si—CH$_3$), 0.927 (s, 6H, Si—CH$_3$), 4.05 (s, 1H), 4.428 (s, 2H, —O—CH$_2$) FTIR (ATR): 3311, 3017, 2929, 2858, 2270, 1058 cm$^{-1}$

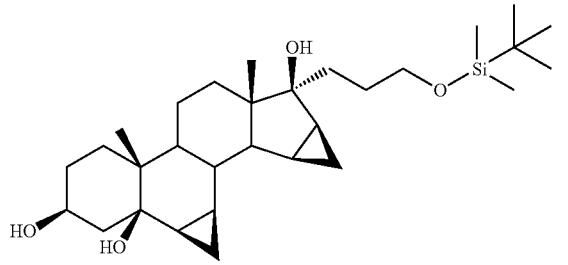

3a

Compound (2a) (5 g, 9.98 mmol) was dissolved in 100 ml of ethyl acetate in a Parr hydrogenation bottle and was mixed with 10% palladium on charcoal (1 g, 0.09 mmol). This mixture was hydrogenated on a Parr apparatus at a pressure of 20 psi for 90 minutes. The catalyst was filtered and washed with ethyl acetate. The solvent was removed in vacuo to afford compound (3a) as a colorless foam (5.01 g, 99%).

NMR (CDCl$_3$) δ 0.0758 (s, 6H, Si—CH$_3$), 0.283 (m, 1H), 0.628 (m, 1H), 0.856 (s, 18-Me), 0.893 (s, 19-Me), 0.918 (s, 9H, Si—CH$_3$), 3.69 (m, 2H), 4.05 (s, 1H). FTIR (ATR): 3374, 3017, 2929, 2858, 1259, 1091, 1049, 835 cm$^{-1}$

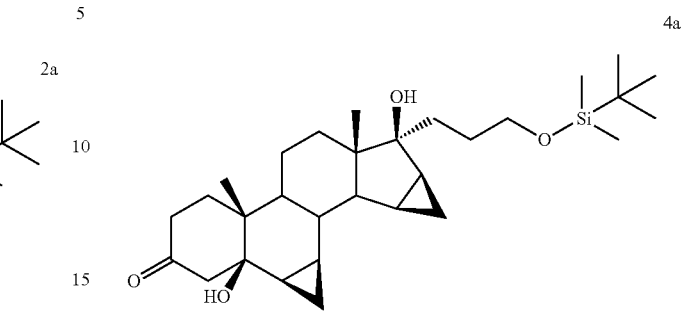

4a

Chromium trioxide (4.95 g, 49.5 mmol) was added to a solution of pyridine (7.83 g, 99.05 mmol) in anhydrous dichloromethane (100 ml). The resulting mixture was stirred for 15 minutes during which time the color changed to burgundy. A solution of compound (1a) (5 g, 9.90 mmol) in 50 ml of dichloromethane was added and the mixture was stirred at room temperature for 6 h. The excess oxidizing agent was quenched by adding isopropanol. The reaction mixture was diluted with MTBE (50 ml) and was passed through a short pad of Celite. The solid was washed again with 2:1 MTBE-CH$_2$Cl$_2$ (50 ml x2). The solvent was removed in vacuo to give a residue which was dissolved in 100 ml of EtOAc, was washed with water, and dried over anhydrous sodium sulfate. The solvent was removed in vacuo to afford compound (4a) as a pale yellow foam (4.5 g, 90.3%).

NMR (CDCl$_3$) δ 0.08 (s, 6H, Si—CH$_3$), 0.31 (m, 1H), 0.914 (s, 9H, Si—CH$_3$), 0.931 (s, 6H, 18-Me, 19-Me) 3.70 (m, 2H). FTIR (ATR): 3399, 3022, 2950, 2929, 2862, 1708, 1649, 1259, 1041 cm$^{-1}$

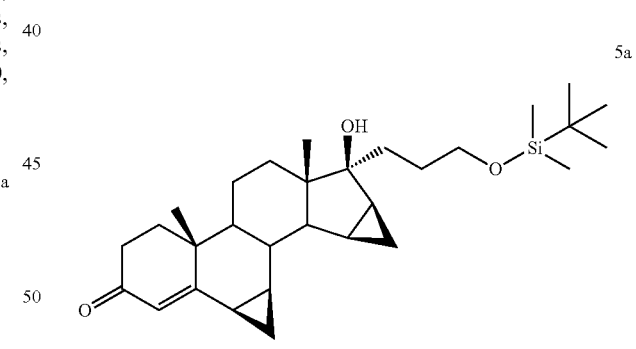

5a

A solution of compound (4a) (5 g, 9.94 mmol) in 50 ml of MeOH was refluxed with NaOH (397 mg, 9.94 mmol) for 3 h. When the reaction was over, as shown by TLC, the reaction mixture was cooled to room temperature and added to ice cold water (150 ml). The mixture was extracted with ethyl acetate (3×50 mL). The combined EtOAc layers were washed with water (100 ml) brine (50 ml) and dried over sodium sulfate. The solvent was removed in vacuo to afford compound (5) as a colorless amorphous solid (4.5 g, 92%).

NMR (CDCl$_3$) δ 0.05 (s, 6H, Si—CH$_3$), 0.296 (m, 1H), 0.886 (s, 9H, Si—CH$_3$), 0.908 (s, 3H, 18-Me), 1.07 (s, 3H, 19-Me), 3.68 (m, 2-H), 5.95 (s, 1H). FTIR (ATR): 3450, 3009, 2950, 2858, 1653, 1603, 1095 cm$^{-1}$

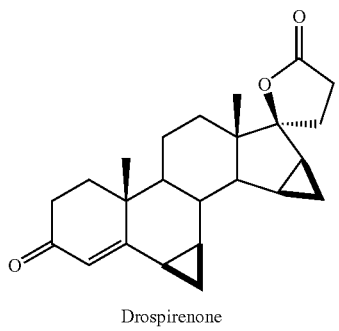

Drospirenone

A solution of compound (5a) (5 g, 9.94 mmol) in 30 ml of acetone was cooled to −15 C as a 2.7M solution of Jones reagent (3.68 ml, 9.94 mmol) was added drop wise. The reaction mixture was stirred at 0 C for 2 h, during this time TLC showed completion of the reaction. The reaction was quenched by adding isopropanol and diluted with water. The reaction mixture was extracted with EtOAc. The combined EtOAc layers were washed with water, sat. $NaHCO_3$ and brine. The EtOAc layers were dried over sodium sulfate and solvent was removed by vacuum to afford crude drospirenone as a pale yellow foam (3 g, 82%) Recrystallization from acetone-hexane gave 1.5 g of pure drospirenone as white solid.

NMR ($CDCl_3$) δ 0.0548 (m, 1H), 0.88 (m, 1H), 1.008 (s, 3H, 18-Me), 1.11 (s, 3H, 18-Me), 6.03 (s, 1H). FTIR (ATR): 3025, 2971, 2942, 1763, 1654, 1590, 1186 cm$^{-1}$

FIG. 2

Experimental Example

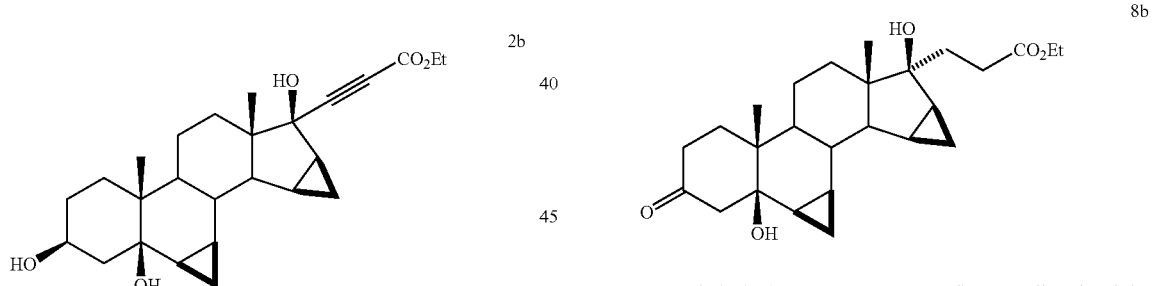

2b

Lithium hexamethyldisilylamide (LiHMDS) 1.0 M/THF (75.7 mL, 75.7 mmol) was introduced into a 500 mL, 3-neck flask equipped with an addition funnel and a pierced septa for the introduction of a thermocouple probe. The mixture was diluted with THF (25 mL). The solution was stirred (Teflon paddle) and chilled to an internal temperature of −72° C. A THF (75 mL) solution of ketodiol (5 g, 15.13 mmol) containing ethyl propiolate (3.07 mL, 30.26 mmol) was added dropwise over 1 hour while not allowing the temperature to rise above −65° C. Upon completion of the addition the mixture was stirred for 3 hrs while allowing the temperature to warm slowly to −60° C. Finally, the mixture was warned to −40° C. over 1 hour.

The mixture was quenched through the addition of acetic acid (4.25 mL)/water (5.0 mL) followed by the addition of saturated ammonium chloride solution (100 mL). The mixture was stirred for 3 min and then transferred to a separatory funnel. The layers were separated and the upper, THF layer was diluted with ethyl acetate (75 mL). The organic phase was washed with water (3×100 mL) and brine (1×100 mL). All the aqueous washes were extracted with ethyl acetate (2×30 mL). The combined organic extract was dried over sodium sulfate, filtered, and evaporated in vacuo (45° C.) to afford a thick oil. Dichloromethane (ca. 35 mL) was added and evaporated in vacuo. The flask was cooled slightly and dichloromethane (33 ml) was added to give a solid mass. The solid was broken up and stirred until a homogeneous slurry was obtained. Hexanes (35 mL) was added slowly to the stirred mixture and the mixture was stored at 2-4 C overnight. The solid was filtered, washed with 30% dichloromethane/hexanes, and dried in vacuo at ambient temperature for 4 hours to give (2b) 5.86 g (90.4%) of a white powder.

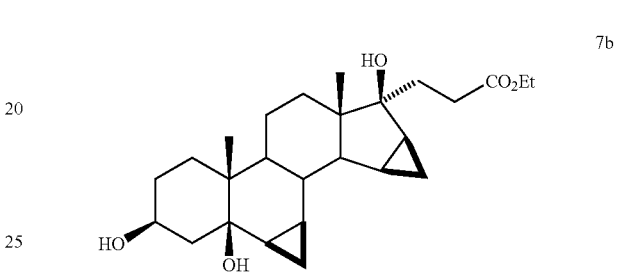

7b

Compound (2b) (5.0 g, 11.67 mmol) was dissolved in THF (50 mL) and 5% Pd/C (622 mg, 0.29 mmol Pd) was added and the mixture was shaken at 15 psi $H_2$ for 2 hours. The mixture was diluted with ethyl acetate (25 mL) and filtered through a pad of Celite. The filter pad was washed with ethyl acetate (3×25 mL) and the filtrate was evaporated to dryness to afford 5.0 g (99.1%) of triol (7b) as a stable foam.

8b

Compound (7a) (5.0 g, 11.56 mmol) was dissolved in dichloromethane (50 mL) and the solution was stirred vigorously and chilled to −15° C. (NaCl/ice) and TEMPO (45.16 mg, 0.29 mmol, 2.5 mol %) was added. The mixture was treated dropwise over about 15-20 min. with a mixture of sodium hypochlorite (12.5%) (11.17 mL, 23.12 mmol) in water (8.0 mL) containing potassium bicarbonate (833 mg, 8.32 mmol). The mixture was allowed to warm to 0 C for 1.25 hrs. Analysis of the reaction by TLC (60% EtOAc/hex) shows the appearance of a slightly less polar product ($\Delta R_f$=0.8 cm). The mixture was chilled to −5 C and was quenched through the dropwise addition (ca 10-15 min) of a water (15.0 mL) solution of sodium phosphate (1.27 g, 7.75 mmol) and sodium metabisulfite (1.10 g, 5.78 mmol). The layers were separated and the dichloromethane solution was washed with water (2×) and brine. All aqueous washes were extracted with additional dichloromethane (2×15 mL). The combined dichloromethane extract was dried over sodium sulfate, filtered, and evaporated to give 4.88 g (98.08%) of ketone (8b) as a stable foam.

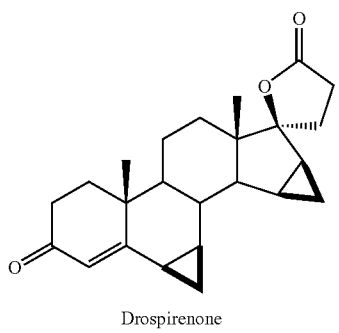

Drospirenone

Compound (8b) was added to a methanol (10 mL) solution containing 8.0 M KOH solution (6.3 mL, 50.36 mmol) preheated to 60 C. The solution was heated at reflux for 2.5 hours. The mixture was chilled in an ice bath and treated with acetic acid (36 mL) and water (5.0 mL). The solution was stirred at 50-60 C for 15 hours. The volatiles were evaporated in vacuo and the acetic acid solution was poured into cold water (150 mL) to give a white precipitate. The aqueous mixture was extracted with ethyl acetate (2×100 mL). The ethyl acetate extracts were washed with water (2×), saturated sodium bicarbonate solution, and brine. The combined ethyl acetate extract was dried over sodium sulfate. Evaporation of the solvent gave a yellow foam. Trituration of the foam with acetone/hexane followed by evaporation gave 4.27 g (92.62%) of a light yellow solid. Recrystallization of the solid from acetone/hexanes gave 3.07 g of drospirenone with an HPLC purity of 99.66%. Evaporation of the mother liquor and recrystallization of the residue affords an additional 0.54 g of slightly impure drospirenone.

FIG. 3

Experimental Example

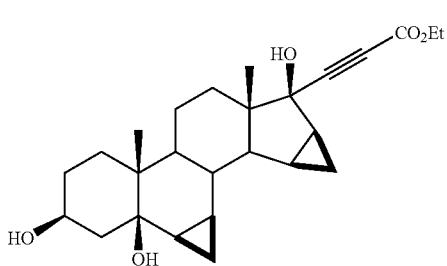

Lithium hexamethyldisilylamide (LiHMDS) 1.0 M/THF (75.7 mL, 75.7 mmol) was introduced into a 500 mL, 3-neck flask equipped with an addition funnel and a pierced septa for the introduction of a thermocouple probe. The mixture was diluted with THF (25 mL). The solution was stirred (Teflon paddle) and chilled to an internal temperature of −72° C. A THF (75 mL) solution of ketodiol (5 g, 15.13 mmol) containing ethyl propiolate (3.07 mL, 30.26 mmol) was added dropwise over 1 hour while not allowing the temperature to rise above −65° C. Upon completion of the addition the mixture was stirred for 3 hrs while allowing the temperature to warm slowly to −60° C. Finally, the mixture was warmed to −40° C. over 1 hour.

The mixture was quenched through the addition of acetic acid (4.25 mL)/water (5.0 mL) followed by the addition of saturated ammonium chloride solution (100 mL). The mixture was stirred for 3 min and then transferred to a separatory funnel. The layers were separated and the upper, THF layer was diluted with ethyl acetate (75 mL). The organic phase was washed with water (3×100 mL) and brine (1×100 mL). All the aqueous washes were extracted with ethyl acetate (2×30 mL). The combined organic extract was dried over sodium sulfate, filtered, and evaporated in vacuo (45° C.) to afford a thick oil. Dichloromethane (ca. 35 mL) was added and evaporated in vacuo. The flask was cooled slightly and dichloromethane (33 ml) was added to give a solid mass. The solid was broken up and stirred until a homogeneous slurry was obtained. Hexanes (35 mL) was added slowly to the stirred mixture and the mixture was stored at 2-4 C overnight. The solid was filtered, washed with 30% dichloromethane/hexanes, and dried in vacuo at ambient temperature for 4 hours to give (2c) 5.86 g (90.4%) of a white powder.

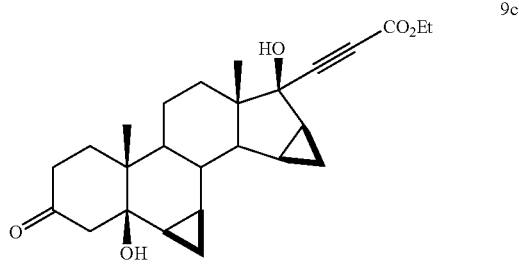

Propiolate adduct (2c) (5.86 g, 13.67 mmol) was suspended in dichloromethane (60 mL). The mixture was stirred vigorously and chilled to −15° C. (NaCl/ice) and TEMPO (54 mg, 0.35 mmol, 2.5 mol %) was added. The mixture was treated dropwise over about 15-20 min. with a mixture of sodium hypochlorite (12.5%) (13.2 mL, 27.34 mmol) in water (8.0 mL) containing potassium bicarbonate (985 mg, 9.84 mmol). During the addition of the hypochlorite solution, a 5-8 C temperature rise was observed and the mixture became yellow. The mixture was allowed to warm to at 0 C for 2 hrs. Analysis of the reaction by TLC (60% EtOAc/hex) shows the appearance of a slightly less polar product ($\Delta R_f$=0.8 cm). The mixture was chilled to −5 C and was quenched through the dropwise addition (ca 10-15 min) of a water (150 mL) solution of sodium phosphate (1.50 g, 9.16 mmol) and sodium metabisulfite (1.30 g, 6.84 mmol). Once again, a temperature rise of 5-8 C was observed and the yellow color was quenched. The layers were separated and the dichloromethane solution was washed with water (2×) and brine. All aqueous washes were extracted with additional dichloromethane (2×15 mL). The combined dichloromethane extract was dried over sodium sulfate and the bulk of the solvent was evaporated in vacuo. Upon the observation of solids in the mixture during the evaporation, the evaporation was discontinued and the residue in the flask diluted with MTBE (35 mL). While stirring, the mixture was slowly diluted with hexanes (35 mL). The mixture was then chilled in an ice bath for 30 min. The solid was filtered, washed with 25% MTBE/hexane, and dried to give intermediate (9c) (4.98 g, 85.31%) as a white solid.

NMR (CDCl$_3$) δ 0.462 (q, 1H), 0.699 (m, 1H), 0.924 (s, 18-Me), 0.952 (s, 19-Me), 1.338 (t, J=7 Hz, OCH$_2$CH$_3$), 2.517 (d, 1H), 3.021 (d, 1H), 4.269 (t, OCH$_2$CH$_3$) ppm. FTIR (ATR): 3493, 3252, 2948, 2226, 1697, 1241 cm$^{-1}$.

23

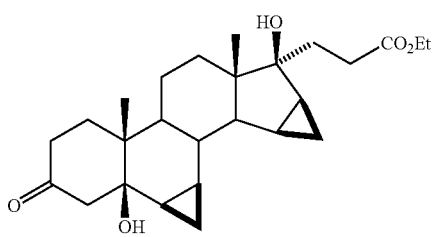

8c

Alkynyl ketone (9c) (5.37 g, 12.59 mmol) was dissolved in THF (27 mL) in a 250 mL shaker bottle. 5% Pd/C (670 mg, 2.5 mol %) was added to the solution and the mixture was shaken under a hydrogen pressure of 15 psi. Over approximately 30 min, there was observed a rapid up take of hydrogen. The pressure was continually adjusted to 15 psi until the uptake of hydrogen ceased and was shaken for a total of 1.5 hrs. The mixture was diluted with a small amount of methanol and filtered through Celite. The filter pad was washed with methanol (ca. 3×25 mL).

NMR (CDCl$_3$) δ 0.353 (q, 1H), 0.704 (m, 2H), 0.930 (s, 18-Me), 0.933 (s, 19-Me), 1.279 (t, J=7 Hz, OCH$_2$CH$_3$), 2.480 (d, 1H), 2.672 (m, 2H), 3.981 (d, 1H), 4.162 (t, OC$\underline{H}_2$CH$_3$) ppm. FTIR (ATR): 345, 2946, 1712, cm$^{-1}$.

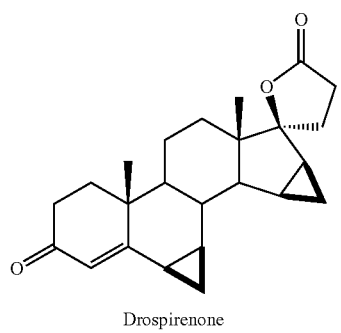

Drospirenone

The filtrate containing compound (8c) described above, was added in one portion to a methanol (10 mL) solution containing 8.0 M KOH solution (6.3 mL, 50.36 mmol) preheated to 60 C. The solution was heated at reflux for 2.5 hours. The mixture was chilled in an ice bath and treated with acetic acid (36 mL) and water (5.0 mL). The solution was stirred at 50-60 C for 15 hours. The volatiles were evaporated in vacuo and the acetic acid solution was poured into cold water (150 mL) to give a white precipitate. The aqueous mixture was extracted with ethyl acetate (2×100 mL). The ethyl acetate extracts were washed with water (2×), saturated sodium bicarbonate solution, and brine. The combined ethyl acetate extract was dried over sodium sulfate. Evaporation of the solvent gave a yellow foam. Trituration of the foam with acetone/hexane followed by evaporation gave 4.27 g (92.62%) of a light yellow solid. Recrystallization of the solid from acetone/hexanes gave 3.07 g of drospirenone with an HPLC purity of 99.66%. Evaporation of the mother liquor and recrystallization of the residue affords an additional 0.54 g of slightly impure drospirenone.

24

FIG. 4

Experimental Example

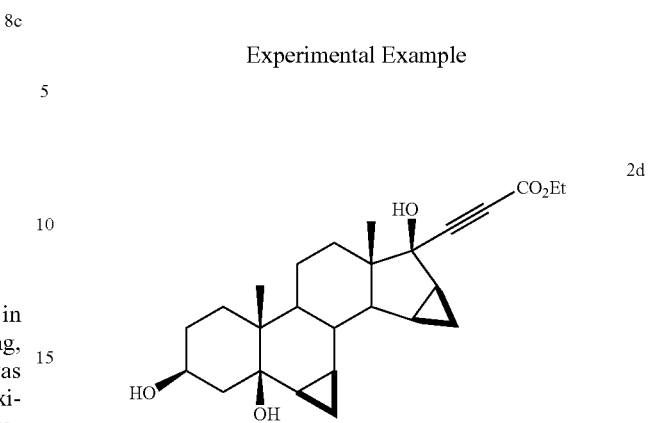

2d

Lithium hexamethyldisilylamide (LiHMDS) 1.0 M/THF (75.7 mL, 75.7 mmol) was introduced into a 500 mL, 3-neck flask equipped with an addition funnel and a pierced septa for the introduction of a theiniocouple probe. The mixture was diluted with THF (25 mL). The solution was stirred (Teflon paddle) and chilled to an internal temperature of −72° C. A THF (75 mL) solution of ketodiol (5 g, 15.13 mmol) containing ethyl propiolate (3.07 mL, 30.26 mmol) was added dropwise over 1 hour while not allowing the temperature to rise above −65° C. Upon completion of the addition the mixture was stirred for 3 hrs while allowing the temperature to warm slowly to −60° C. Finally, the mixture was warmed to −40° C. over 1 hour.

The mixture was quenched through the addition of acetic acid (4.25 mL)/water (5.0 mL) followed by the addition of saturated ammonium chloride solution (100 mL). The mixture was stirred for 3 min and then transferred to a separatory funnel. The layers were separated and the upper, THF layer was diluted with ethyl acetate (75 mL). The organic phase was washed with water (3×100 mL) and brine (1×100 mL). All the aqueous washes were extracted with ethyl acetate (2×30 mL). The combined organic extract was dried over sodium sulfate, filtered, and evaporated in vacuo (45° C.) to afford a thick oil. Dichloromethane (ca. 35 mL) was added and evaporated in vacuo. The flask was cooled slightly and dichloromethane (33 ml) was added to give a solid mass. The solid was broken up and stirred until a homogeneous slurry was obtained. Hexanes (35 mL) was added slowly to the stirred mixture and the mixture was stored at 2-4 C overnight. The solid was filtered, washed with 30% dichloromethane/hexanes, and dried in vacuo at ambient temperature for 4 hours to give (2d) 5.86 g (90.4%) of a white powder.

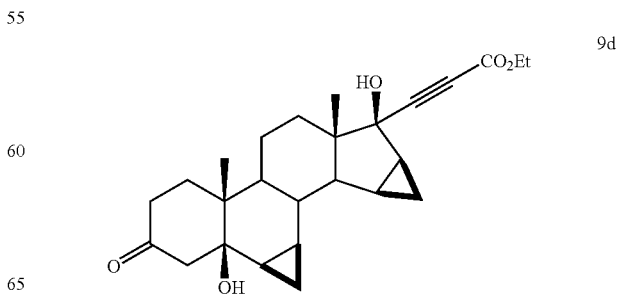

9d

Propiolate adduct (2d) (5.86 g, 13.67 mmol) was suspended in dichloromethane (60 mL). The mixture was stirred vigorously and chilled to −15° C. (NaCl/ice) and TEMPO (54 mg, 0.35 mmol, 2.5 mol %) was added. The mixture was treated dropwise over about 15-20 min. with a mixture of sodium hypochlorite (12.5%) (13.2 mL, 27.34 mmol) in water (8.0 mL) containing potassium bicarbonate (985 mg, 9.84 mmol). During the addition of the hypochlorite solution, a 5-8 C temperature rise was observed and the mixture became yellow. The mixture was allowed to warm to at 0 C for 2 hrs. Analysis of the reaction by TLC (60% EtOAc/hex) shows the appearance of a slightly less polar product ($\Delta R_f$=0.8 cm). The mixture was chilled to −5 C and was quenched through the dropwise addition (ca 10-15 min) of a water (15.0 mL) solution of sodium phosphate (1.50 g, 9.16 mmol) and sodium metabisulfite (1.30 g, 6.84 mmol). Once again, a temperature rise of 5-8 C was observed and the yellow color was quenched. The layers were separated and the dichloromethane solution was washed with water (2×) and brine. All aqueous washes were extracted with additional dichloromethane (2×15 mL). The combined dichloromethane extract was dried over sodium sulfate and the bulk of the solvent was evaporated in vacuo. Upon the observation of solids in the mixture during the evaporation, the evaporation was discontinued and the residue in the flask diluted with MTBE (35 mL). While stirring, the mixture was slowly diluted with hexanes (35 mL). The mixture was then chilled in an ice bath for 30 min. The solid was filtered, washed with 25% MTBE/hexane, and dried to give intermediate (9d) (4.98 g, 85.31%) as a white solid.

NMR (CDCl$_3$) δ 0.462 (q, 1H), 0.699 (m, 1H), 0.924 (s, 18-Me), 0.952 (s, 19-Me), 1.338 (t, J=7 Hz, OCH$_2$CH$_3$), 2.517 (d, 1H), 3.021 (d, 1H), 4.269 (t, OCH$_2$CH$_3$) ppm. FTIR (ATR): 3493, 3252, 2948, 2226, 1697, 1$\overline{21}$ cm$^{-1}$.

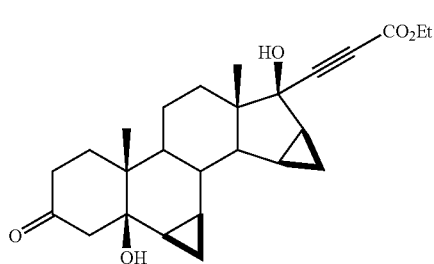

10d

Compound (9d) (5.0 g) was dissolved in methanol (50 mL) and treated with 1.0 N sulfuric acid (10 mL). The mixture was heated to reflux for 3 hours, cooled, and neutralized through the addition of saturated sodium bicarbonate solution. Most of the methanol was evaporated in vacuo at ambient temperature and diluted with water. The aqueous mixture was extracted with ethyl acetate. The ethyl acetate extract was washed with water and brine, dried over sodium sulfate, filtered, and evaporated to give 4.95 g of unsaturated ketone (10d) as a stable foam.

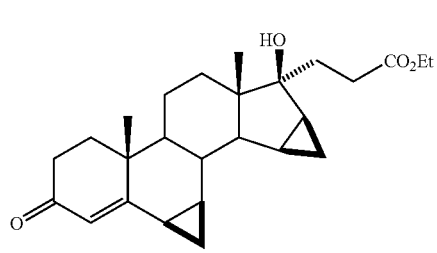

11d

Compound (10d) (5.0 g, 12.24 mmol) was dissolved in degassed benzene (50 mL) and treated with chlorotris(triphenylphosphine)rhodium (I) (283.1 mg, 0.31 mmol and the resulting mixture was stirred in a hydrogen atmosphere for 10 hours. The solution was evaporated, reconstituted in 50% ethyl acetate/hexanes, and passed through a short column of neutral alumina. Evaporation of the solvent gave 4.95 g of (11d) as a stable foam.

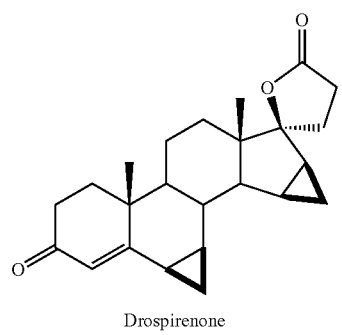

Drospirenone

Compound (11d) (4.95 g, 12.01 mmol) was dissolved in 10% aqueous methanol (50 mL) and solid potassium carbonate (4.98 g, 36.04 mmol) was added. The mixture was stirred at room temperature for 30 min and the bicarbonate was neutralized through the addition of acetic acid (2.06 mL, 36.04 mmol). The methanol was evaporated in vacuo at ambient temperature and diluted with water. The aqueous mixture was extracted with ethyl acetate. The ethyl acetate extract was washed with water and brine, dried over sodium sulfate, filtered, and evaporated to give 4.10 g (93%) of a semi solid. The material was dissolved in dichloromethane and evaporated in vacuo to give a stable foam. The foam was dissolved in ethyl acetate (5 mL) and allowed to stand overnight. The resulting solid was filtered, washed with cold ethyl acetate, and dried in vacuo to afford 2.86 g (66%) of pure drospirenone.

FIG. 5

Experimental Example 1

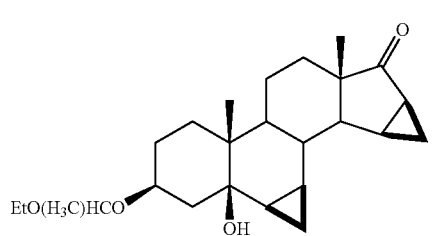

1e

A dichloromethane (50 mL) solution of ketodiol (1) (5.0 g, 15.13 mmol) was treated with ethyl vinyl ether (7.24 mL, 75.65 mmol), followed by the addition of pyridinium tosylate (380 mg, 1.15 mmol). The solution was stirred at room temperature for 30 min. The dichloromethane solution was washed with water (2×), brine, and dried over sodium sulfate. Following filtration, evaporation of the solvent gave 6.14 g of the 3-protected compound (1e) as a stable foam.

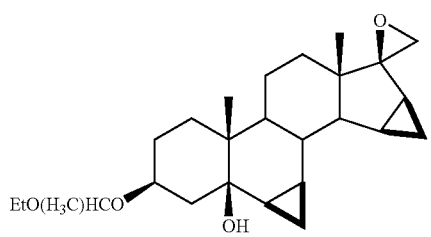

12e

Compound (1e) (6.14 g, 15.13 mmol) was dissolved in DMSO/THF (15 mL/15 mL), treated with trimethylsulfonium iodide (4.63 g, 22.70 mmol) and the mixture was chilled to −15 C. The mixture was treated portion wise with potassium t-butoxide (3.23 g, 28.82 mmol). The mixture was stirred at −15 C for 45 min and then poured into ice/water (200 mL). The aqueous mixture was extracted with ethyl acetate. The ethyl acetate extract was washed with water (2×) and brine, dried over sodium sulfate, and filtered. Evaporation of the solvent gave 6.21 g (98.42%) of oxirane (12e) as a stable foam.

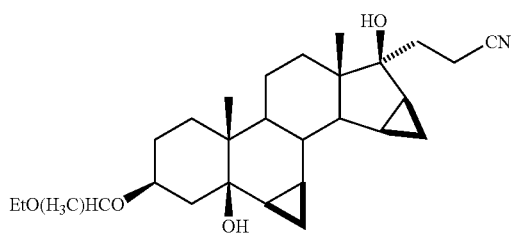

13e

A THF (30 mL) solution of di-isopropyl amine (12.02 mL, 85.03 mmol) was chilled to −40 C and treated with butyl lithium (2.5 M/hexanes, 34.01 mL, 85.03 mmol) and the mixture was stirred for 15 min. A THF (5 mL) solution of acetonitrile (4.7 mL, 90.79 mmol) was added dropwise to the in situ generated lithium di-isopropylamide (LDA) solution to give a slurry of the acetonitrile anion. After stirring for 15 min at −40° C., compound (12e) (6.21 g, 14.91 mmol) as a THF (25 mL) solution was added dropwise over 10 min. The mixture was stirred for 30 min and then quenched through the addition of saturated ammonium chloride solution (210 mL). The mixture was extracted with ethyl acetate. The ethyl acetate extract was washed with water (3×) and brine, dried over sodium sulfate, and filtered. Evaporation of the solvent gave 7.07 g of the addition product (13e) as a tacky foam.

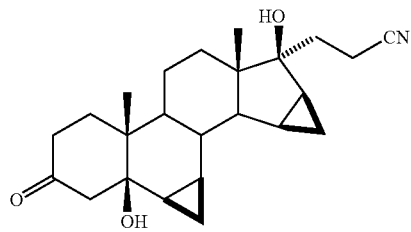

14e

Compound 13e (5.0 g, 10.93 mmol) was dissolved in acetone (25 mL) and chilled to 0 C. The stirred solution was treated dropwise with 2.7M chromic acid (Jones Reagent) (7.0 mL, 18.91 mmol). After 1.5 hrs, the excess Cr (VI) was quenched through the addition of 2-propanol until the green color of Cr (IV) was evident. Water (300 mL) was added and the mixture was stirred until all the chromium salts were dissolved. The aqueous mixture was extracted with ethyl acetate. The ethyl acetate extract was washed with water (2×) and brine, dried over sodium sulfate, and filtered. Evaporation of the solvent gave 3.83 g (96%) of ketone (14e) as a stable foam.

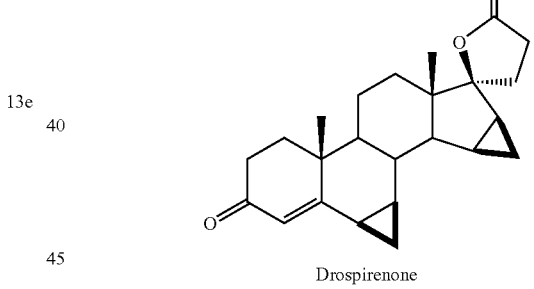

Drospirenone

Compound (14e) (3.83 g, 10.48 mmol) was dissolved in methanol (38 mL) and treated with 8.0 M KOH solution (7.0 mL, 56 mmol) and the mixture was heated at reflux for 5 hours. The mixture was cooled to 0 C and treated with acetic acid (15 mL) and water (6 mL) and the mixture was stirred at 50 C for 6 hours. The solvents were evaporated in vacuo and the residue was diluted with water (200 mL). The aqueous mixture was extracted with ethyl acetate. The ethyl acetate extract was washed with water (2×) and brine, dried over sodium sulfate, and filtered. Evaporation of the solvent gave 3.76 g (94%) of crude drospirenone as a stable foam. The crude drospirenone was dissolved in 60% ethyl acetate/hexanes and passed through a short column of neutral alumina (10× w/w) and the column was eluted with the same solvent. Following evaporation of the solvent, 2.58 g (65%) of crystalline drospirenone was obtained. Recrystallization from acetone/hexanes afforded pure drospirenone.

FIG. 5

Experimental Example 2

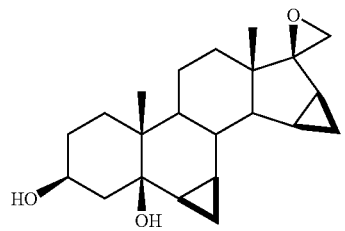

12f

Intermediate (1) (5 g, 15.13 mmol) was dissolved in DMSO/THF (50 mL/50 mL), treated with trimethylsulfonium iodide (4.63 g, 22.70 mmol), and the mixture was chilled to −15 C. The mixture was treated portion wise with potassium t-butoxide (5.03 g, 43.88 mmol). The mixture was stirred at −15 C for 45 min and then poured into ice/water (200 mL). The aqueous mixture was extracted with ethyl acetate. The ethyl acetate extract was washed with water (2×) and brine, dried over sodium sulfate, and filtered. Evaporation of the solvent gave 5.11 g (98%) of oxirane (12f) as a stable foam.

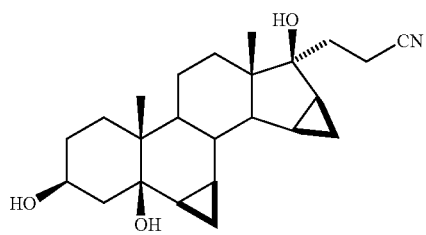

13f

A THF (30 mL) solution of di-isopropyl amine (12.02 mL, 85.03 mmol) was chilled to −40 C and treated with butyl lithium (2.5 M/hexanes, 34.01 mL, 85.03 mmol) and the mixture was stirred for 15 min. A THF (5 mL) solution of acetonitrile (4.7 mL, 90.79 mmol) was added dropwise to the above lithium di-isopropylamide (LDA) solution to give a slurry of the acetonitrile anion. After stirring for 15 min at −40 C, compound (12f) (5.11 g, 14.83 mmol) as a THF (75 mL) solution was added dropwise over 10 min. The mixture was stirred for 30 min and then quenched through the addition of saturated ammonium chloride solution (300 mL). The mixture was extracted with ethyl acetate. The ethyl acetate extract was washed with water (3×) and brine, dried over sodium sulfate, and filtered. Evaporation of the solvent gave 5.75 g of addition product (13f) as a tacky foam.

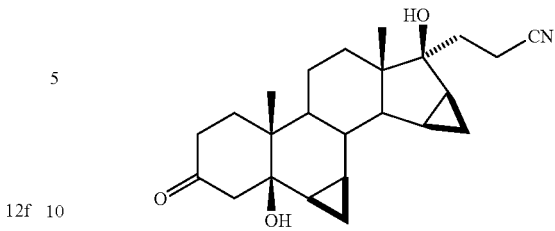

14f

Compound 13f (5.75 g, 14.95 mmol) was dissolved in acetone (25 mL) and chilled to 0 C. The stirred solution was treated dropwise with 2.7M chromic acid (Jones Reagent) until the orange color of Cr (VI) persisted. After 1.5 hrs, the excess Cr (VI) was quenched through the addition of 2-propanol until the green color of Cr (IV) was evident. Water (300 mL) was added and the mixture was stirred until all the chromium salts were dissolved. The aqueous mixture was extracted with ethyl acetate. The ethyl acetate extract was washed with water (2×) and brine, dried over sodium sulfate, and filtered. Evaporation of the solvent gave 5.5 g (96%) of ketone (14f) as a stable foam.

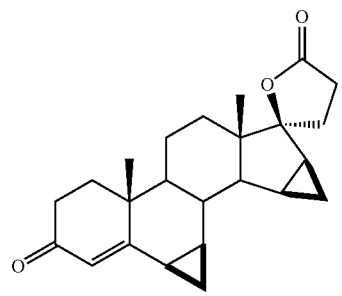

Drospirenone

Compound (14f) (5.5 g, 14.38 mmol) was dissolved in methanol (50 mL) and treated with 8.0 M KOH solution (9.35 mL, 74.77 mmol) and the mixture was heated at reflux for 5 hours. The mixture was cooled to 0 C and treated with acetic acid (25 mL) and water (10 mL) and the mixture was stirred at 50 C for 6 hours. The solvents were evaporated in vacuo and the residue was diluted with water (300 mL). The aqueous mixture was extracted with ethyl acetate. The ethyl acetate extract was washed with water (2×) and brine, dried over sodium sulfate, and filtered. Evaporation of the solvent gave 4.95 g (94%) of crude drospirenone as a stable foam. The crude drospirenone was dissolved in 60% ethyl acetate/hexanes and passed through a short column of neutral alumina (10× w/w) and the column was eluted with the same solvent. Following evaporation of the solvent, 3.43 g (65%) of crystalline drospirenone was obtained. Recrystallization from acetone/hexanes afforded pure drospirenone.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of making drospirenone comprising:

reacting the intermediate (1) with the reactant (–)C≡C—Z, as depicted in the reaction (I) to yield intermediate (2), where each $R^1$, $R^2$ is independently H, $Si(R^5)_3$, $C(R^6)_2(OR^5)$ or $CR^6(OR^5)_2$; Z is CN or $CO_2R^4$; each $R^4$ and $R^5$ is independently hydrogen, alkyl, phenyl, benzyl, or an alkali metal and each $R^6$ is independently alkyl or hydrogen; and

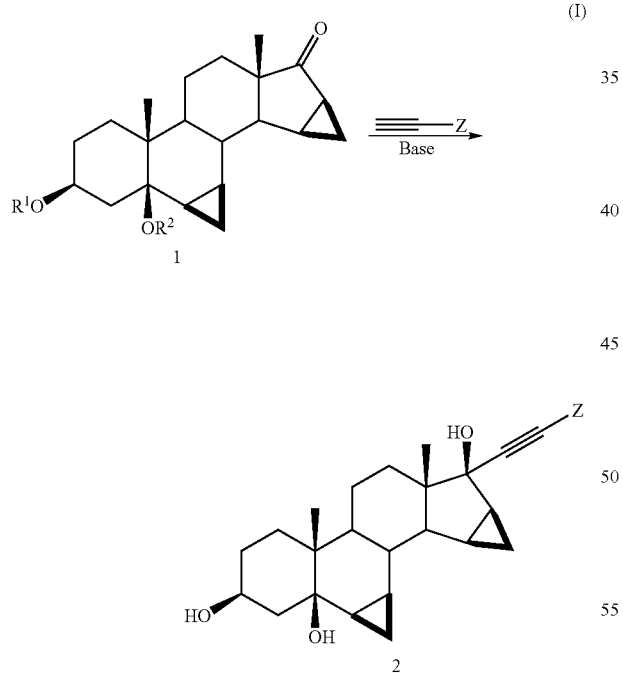

converting intermediate (2) to drospirenone.

2. The method of claim 1, wherein converting the intermediate (2) to drospirenone comprises:

reducing the alkyne functionality of intermediate (2) to form intermediate (3), as depicted in reaction (II);

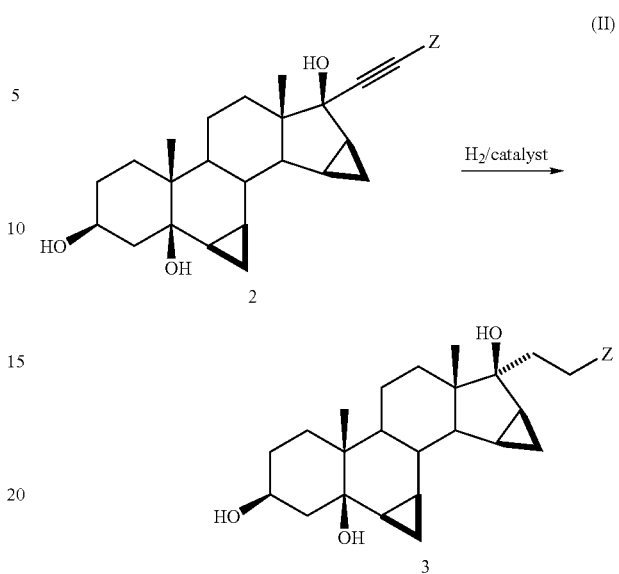

oxidizing intermediate (2) to form intermediate (4), as depicted in reaction (III);

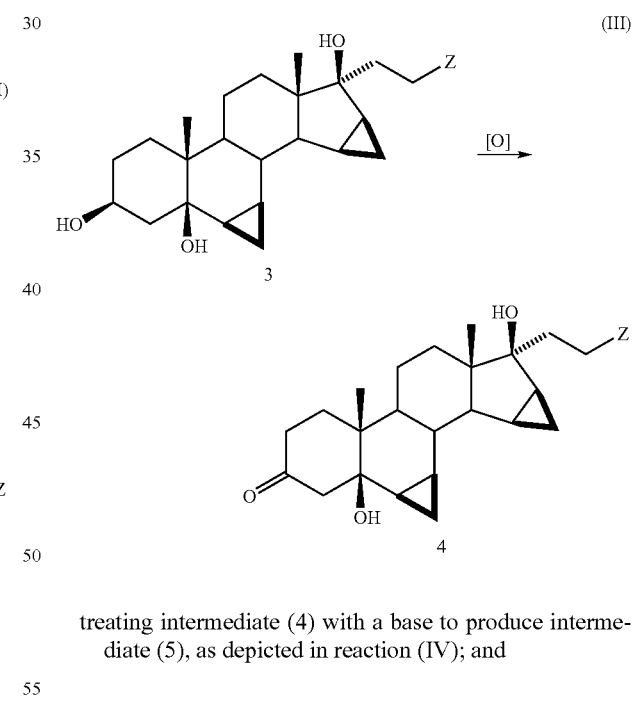

treating intermediate (4) with a base to produce intermediate (5), as depicted in reaction (IV); and

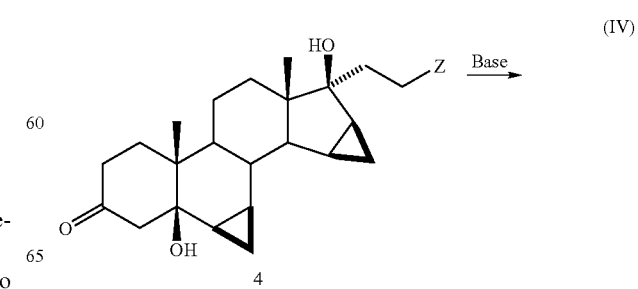

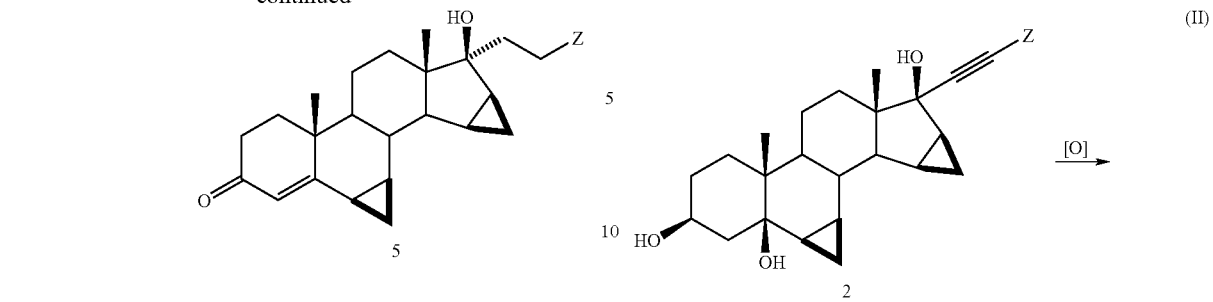

converting the intermediate (5) to drospirenone by forming the spirolactone substitutent, as depicted in reaction (V)

converting the intermediate (9) to drospirenone as depicted in reaction (III)

3. The method of claim 2, wherein the oxidation of reaction (III) is performed using a chromium based oxidation.

4. The method of claim 2, wherein the elimination reaction (IV) is performed using an alkali metal alkyloxide.

5. The method of claim 1, wherein $R^1$ and $R^2$ are H; Z is $CO_2R^4$; and $R^4$ is alkyl.

6. The method of claim 5, wherein in reaction (I) the propargyl alcohol anion is generated by the reaction of HC≡CCO$_2$R with lithium hexamethyldisilylamide.

7. The method of claim 5, wherein the oxidation of reaction (III) is performed using 2,2,6,6-tetramethylpiperidine-1-oxyl.

8. The method of claim 5, wherein the elimination reaction (IV) is performed using an alcoholic alkali hydroxide.

9. The method of claim 5, wherein the conversion of intermediate (5) to drospirenone is performed under conditions.

10. The method of claim 5, wherein the conversion of intermediate (5) to drospirenone is performed using an organic acid.

11. The method of claim 1, wherein reaction (II) is performed using Pd in the presence of hydrogen.

12. The method of claim 1, wherein converting the intermediate (2) to drospirenone comprises:

oxidizing intermediate (2) to form intermediate (9), as depicted in reaction (II);

13. The method of claim 12, wherein $R^1$ and $R^2$ are H; Z is $CO_2R^4$; and $R^4$ is alkyl.

14. The method of claim 13, wherein in reaction (I) the propargyl alcohol anion is generated by the reaction of HC≡CCO$_2$R with lithium hexamethyldisilylamide.

15. The method of claim 13, wherein the oxidation of reaction (II) is performed using 2,2,6,6-tetramethylpiperidine-1-oxyl.

16. The method of claim 13, wherein the conversion of intermediate (9) to drospirenone comprises:

reducing the akyne functionality of intermediate (9) to form intermediate (8), as depicted in reaction (IV); and (IV)

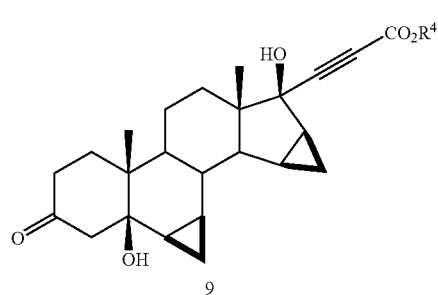

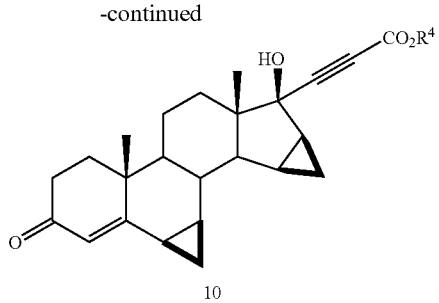

reducing the akyne functionality of intermediate (10) to form intermediate (11), as depicted in reaction (V); and (V)

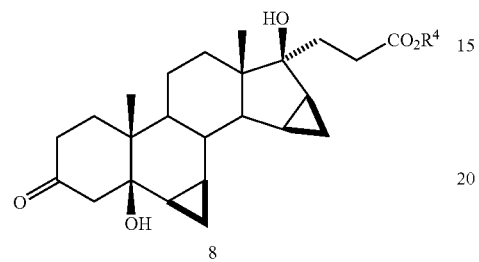

treating intermediate (8) with an aqueous base followed by an aqueous acid to form drospirenone.

17. The method of claim 16, wherein reaction (IV) is performed using Pd in the presence of hydrogen.

18. The method of claim 13, wherein the conversion of intermediate (9) to drospirenone comprises:

treating intermediate (9) with an aqueous acid to produce intermediate (10), as depicted in reaction (IV); and (IV)

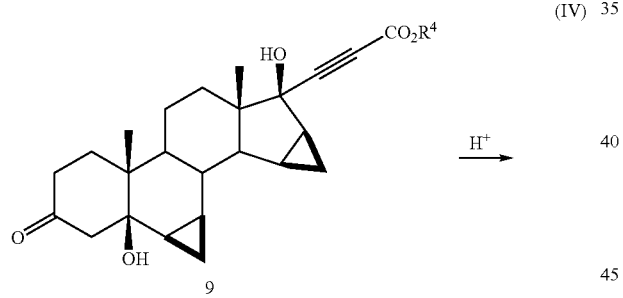

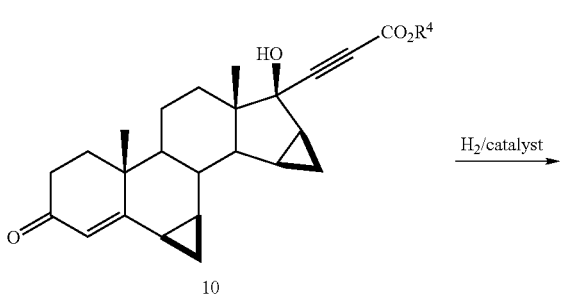

treating intermediate (11) with an aqueous base followed by an aqueous acid to form drospirenone.

19. The method of claim 18, wherein reaction (V) is performed using Rh in the presence of hydrogen.

* * * * *

UNITED STATES PATENT AND TRADEMARK OFFICE
CERTIFICATE OF CORRECTION

PATENT NO. : 8,334,375 B2
APPLICATION NO. : 12/752859
DATED : December 18, 2012
INVENTOR(S) : Nickisch et al.

Page 1 of 1

It is certified that error appears in the above-identified patent and that said Letters Patent is hereby corrected as shown below:

In the Claims:

Claim 2, col. 32, line 26, please delete "(2)" and substitute therefor -- (3) --.

Signed and Sealed this
Second Day of April, 2013

Teresa Stanek Rea
*Acting Director of the United States Patent and Trademark Office*